United States Patent [19]

Wong

[11] Patent Number: 5,759,825
[45] Date of Patent: *Jun. 2, 1998

[54] METHOD FOR SYNTHESIZING 2-KETOALDONIC ACIDS

[75] Inventor: Chi-Huey Wong, Rancho Sante Fe, Calif.

[73] Assignee: The Scripps Research Institute, La Jolla, Calif.

[*] Notice: The term of this patent shall not extend beyond the expiration date of Pat. No. 5,358,859.

[21] Appl. No.: 475,777

[22] Filed: Jun. 7, 1995

Related U.S. Application Data

[60] Continuation-in-part of Ser. No. 328,739, Oct. 25, 1994, Pat. No. 5,585,261, which is a division of Ser. No. 993,140, Dec. 18, 1992, Pat. No. 5,358,859, and a continuation-in-part of Ser. No. 946,546, Sep. 17, 1992, which is a continuation-in-part of Ser. No. 763,359, Sep. 20, 1991, Pat. No. 5,162, 513.

[51] Int. Cl.$^6$ ............... C12P 7/40; C12P 19/02; C12N 9/88; C07H 1/00
[52] U.S. Cl. ............. 435/136; 435/105; 435/232; 536/1.11; 536/18.6; 536/124
[58] Field of Search ............... 435/136, 105, 435/232; 536/1.11, 18.6, 124

[56] References Cited

U.S. PATENT DOCUMENTS

| 5,358,859 | 10/1994 | Wong et al. | 435/105 |
| 5,585,261 | 12/1996 | Wong et al. | 435/232 |

FOREIGN PATENT DOCUMENTS

| 9306227 | 4/1993 | WIPO | C12P 19/02 |

OTHER PUBLICATIONS

Liu et. al. J. Am. Chem. Soc. 1992, 114, 3901–3910.
Kim et. al. J. Am. Chem. Soc. 1988, 110, 6481–6486.
Whitesides et. al. Angew. Chemie. 1985, 24, 617–718.
Toone et. al. Tetrahedron 1989, 45, 5365–5422.

*Primary Examiner*—Marian C. Knode
*Assistant Examiner*—Ali R. Salimi
*Attorney, Agent, or Firm*—Donald G. Lewis

[57] ABSTRACT

2-Ketoaldonic acid is synthesized by aldolase condensation reaction involving pyruvate and an aldose acceptor in the presence of excess pyruvate. After the reaction is substantially complete, the excess pyruvate is removed from the reaction mixture by treatment with pyruvate decarboxylase.

21 Claims, No Drawings

METHOD FOR SYNTHESIZING 2-KETOALDONIC ACIDS

CROSS-REFERENCE TO RELATED APPLICATIONS

This is a continuation-in-part of U.S. application Ser. No. 08/328,739, filed Oct. 25, 1994, now U.S. Pat. No. 5,585,261 which is a divisional of application Ser. No. 07/993,140, filed Dec. 18, 1992, issued Nov. 25, 1994, now U.S. Pat. No. 5,358,859 and is also a continuation-in-part of application Ser. No. 07/946,546, filed Sep. 17, 1992, which is a continuation-in-part of application Ser. No. 07/763,359, filed Sep. 20, 1991, now U.S. Pat. No. 5,162,513.

GOVERNMENT RIGHTS

This invention was made with government support under Grant No. GM 44154 awarded by the National Institutes of Health. The U.S. government has certain rights in the invention.

TECHNICAL FIELD OF THE DESCRIPTION

The present invention relates to enzymatic methods for synthesizing 2-ketoaldonic acids employing both aldolase and pyruvate decarboxylase.

BACKGROUND OF THE INVENTION

An aldose is a sugar represented by the following structure, viz.: $CH_2OH-(CHOH)_n-CHO$. An aldonic acid is a sugar derivative formed by oxidizing an aldose to produce a compound represented by the following structure, viz.: $CH_2OH-(CHOH)_n-COOH$. The carboxylic acid defines the C(1) position of aldonic acid. A 2-ketoaldonic acid is a sugar derivative represented by the following structure, viz.: $CH_2OH-(CHOH)_{n-1}-CO-COOH$, i.e., the 2-ketoaldonic acid includes a carbonyl group at the C(2) position. The present invention is directed to the synthesis of 2-ketoaldonic acids and 2-ketoaldonic acid derivatives. 2-Ketoaldonic acid derivatives include deoxy derivatives and conventional sugar substituents at positions other than the C(1) and C(2) positions.

2-Ketoaldonic acids are conventionally synthesized by an aldolase catalyzed aldol condensation reaction involving pyruvate and an aldose. The enzyme catalyzed aldol reaction proceeds through two steps represented as follows:

Enzyme +

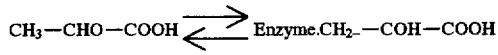

then

Enzyme.CH$_2$—COH—COOH +

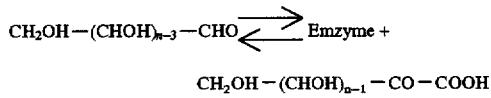

$CH_2OH-(CHOH)_{n-1}-CO-COOH$

In the first step, pyruvate is bound to the aldolase enzyme and undergoes an enolization reaction. In the second step, the nucleophilic enol attacks the carbonyl group of the aldose to form a condensation product, viz. 2-ketoaldonic acid.

Each of the above steps involves an equilibrium reaction. In each case, the forward reaction is favored by addition of an excess of pyruvate. Unfortunately, it can be difficult to isolate the product from the excess of pyruvate. What is needed is a method for producing 2-ketoaldonic acid using the aldolase condensation reaction wherein the product is not contaminated by an excess of pyruvate.

BRIEF SUMMARY OF THE INVENTION

The invention is directed to an enhanced process for synthesizing 2-ketoaldonic acids. In accordance with this process, the following are admixed:

1. a catalytic amount of an aldolase, wherein the aldolase is of a type which can employ pyruvate as a donor molecule;
2. an excess of pyruvate, e.g. about 2 to about 10 fold excess; and
3. an acceptor substrate aldose, wherein the aldose is of a type which is employable with the aldolase as an acceptor.

The above three items are admixed in an aqueous solvent to form a reaction mixture. That reaction mixture is maintained for a time period and under biological reaction conditions sufficient for the condensation of the pyruvate with the acceptor substrate aldose to form a ketoaldonic acid.

After the above reaction is substantially complete, the enzyme pyruvate decarboxylase is then added to the reaction mixture and the resulting composition is maintained as above until the excess pyruvate is decomposed. This addition preferably occurs after denaturation of the aldolase as by acidification or other means. Denaturation of the aldolase prior to the addition of decarboxylase prevents the loss of product due to an aldolase catalyzed back reaction. The pyruvate decarboxylase can be added as the purified enzyme or as whole acid-free baker's yeast cells. The ketoaldonic acid is thereafter recovered by standard procedures that include a separation from the yeast cells, where used.

DETAILED DESCRIPTION OF THE INVENTION

The invention is directed to an improved process for the synthesis of 2-ketoaldonic acids.

An excess of pyruvate, typically about a 2- to about 10-fold excess, is admixed in an aqueous solvent with a catalytic amount of aldolase and an acceptor substrate for that enzyme to form a reaction mixture. The reaction mixture is maintained for a time period and under biological reaction conditions sufficient to condense the pyruvate and acceptor substrate to form a 2-ketoaldonic acid product. Specific exemplary aldolases and acceptor substrates are noted in the Examples section below. Additional aldolases and aldose acceptor substrates for various aldolases are discussed before and are discussed in Wong, C-H., *Microbial aldolases in Enzymes in Carbohydrate Synthesis*, ed. by Bednarski and Simon, American Chemical Society, ACS Symposium Series No. 466 (1991). Non-substrates are also discussed. Whether an aldose is an acceptor substrate for a particular aldolase can be readily ascertained by admixture with excess pyruvate, the enzyme and potential acceptor substrate aldose as discussed herein, followed by maintenance as discussed herein, e.g. 2–3 days. Analysis of the reaction mixture as by thin layer chromatography indicates whether an 2-ketoaldonic acid has been formed.

After the 2-ketoaldonic acid has formed, a catalytic amount of pyruvate decarboxylase is admixed to the aqueous solvent medium and the resulting admixture is maintained as before, but using a pH value of about 5.5 to about 6.5, until the pyruvate has decomposed. This step is utilized because it has been found that the excess pyruvate utilized in the condensation reaction interferes with recovery of the 2-ketoaldonic acid product. Thus, for example, in previously reported procedures for the isolation of enzymatically produced sialic acid (Kim et al., *J. Am. Chem. Soc.*, 110:6481 (1988) and Liu et al., *J. Am. Chem. Soc.*, 114:3901 (1992)) a repetitive extraction of pyruvic acid with ethyl acetate under acidic conditions was used. Under those conditions, the pyruvate exists mainly as the hydrated form in the aqueous phase where its presence makes isolation of aldonic acid difficult.

The pyruvate decarboxylase (EC 4.1.1.1) is preferably admixed after denaturation of the aldolase. That enzyme is conveniently denatured by adjusting the solution pH value to about 2 and maintaining the pH value for about one hour.

The pyruvate decarboxylase can be provided as a purified enzyme as is available from Sigma Chemical Co. at $80.00 per 100 Units. That enzyme can also be provided by culturing baker's yeast cells. Baker's yeast cells are much less costly, e.g. $16.00 per 500 g from Sigma. The baker's yeast cells must be acid-free, which can be accomplished by washing the cells as described hereinafter.

After the excess pyruvate has been decomposed, the 2-ketoaldonic acid is recovered by usual techniques such as by ion exchange chromatography or crystallization. Where baker's yeast cells are used as the source of the pyruvate decarboxylase, the cells are removed as by centrifugation prior to use of ion exchange or other techniques. Exemplary procedures for recovery of the aldonic acids are illustrated hereinafter.

Pyruvate is readily available from commercial sources (Sigma Chemical Co., St. Louis, Mo.). A preferred formulation of pyruvate is sodium pyruvate. Pyruvate is typically used in an amount in excess of the one mole required for the reaction to drive the reaction to completion. A 2- to about 10-fold excess is usually used.

As used herein, the phrase "catalytic amount" means that amount of aldolase at least sufficient to catalyze, in a non-rate limiting manner, the condensation of pyruvate and acceptor substrate to product. More than a catalytic amount can be used.

The catalytic amount of aldolase varies according to the specific activity of aldolase (Units/mg), the concentration of acceptor substrate as well as biological reaction conditions such as temperature, time and pH value. Means for determining the catalytic amount of aldolase under preselected substrate concentrations and biological reaction conditions are well known to those of skill in the art. Typical amounts range from about 5 to about 20 Units (U) per millimole (mmol) of acceptor substrate, with about 10 to about 15 U/mmol typically being used.

Each ingredient is admixed with each of the other ingredients in a suitable aqueous solvent to form a reaction mixture. The reaction mixture is maintained under biological reaction conditions (temperature, pH, solvent osmolality, ionic composition and ambient pressure) for a period of time sufficient to condense the substrate acceptor and pyruvate to form a product.

Temperature can range from about 15° C. to about 40° C. Preferably, temperature is from about 20° C. to about 40° C. and, more preferably from about 25° C. to about 37° C.

The pH value of the solvent and for maintenance can range from about 6.0 to about 11.0. Preferably, the pH value is from about 6.0 to about 8.5 and, more preferably from about 7.0 to about 7.5. The pH value is maintained by buffers in the aqueous solvent. A preferred buffer is potassium phosphate.

The aqueous solvent preferably further comprises an anti-oxidant. A preferred anti-oxidant is a sulfur-containing reducing agent such as a mercaptan (thiol). Exemplary mercaptans are mercaptoethanol and dithiothreitol.

The reaction time varies with the temperature and the activity of the aldolase. The reaction time for 10 Units of a typical aldolase admixed with an acceptor substrate concentration of about 1 mM and a 10 fold excess of pyruvate at 37° C. is about 48 hours.

Method

A 0.1M solution of aldose (1 mmol) in a 0.05M potassium phosphate buffer (pH 7.4) containing 1 mM dithiothreitol, sodium pyruvate (10 eq), and 10 units of an aldolase is incubated at 37° C. (total volume=10 mL) for three days. For a larger scale synthesis, the aldolase can be used in an immobilized form (Liu et al., *J. Am. Chem. Soc.*, 114:3901 (1991)). The aldolase is of a type which employs pyruvate as a substrate donor and aldose as an substrate acceptor.

The reaction is monitored by TLC (i-PrOH/$H_2O$=7:3 v/v). After the reaction is substantially complete, the mixture is adjusted to pH 2.0 by addition of Dowex® 50W-X8 ($H^+$ form, 20–50 mesh) and incubated for one hour to denature the enzyme; the mixture is then adjusted to pH 6.5 by adding concentrated aqueous ammonia solution.

Baker's yeast is pre-treated separately as follows: Baker's yeast (Sigma type II, YSC-2, 15 g, $16/500 g) is suspended in cold water (200 mL) and the mixture stirred at 4° C. overnight (about 18 hours). The cells are harvested at 10,000 ×g (8,500 r.p.m.) for 30 minutes at 4° C. and washed twice with cold water (100 mL). This procedure is necessary to remove all of the polar acidic materials prior to use.

The collected cells (35 mL) containing pyruvate decarboxylase are then resuspended in water (40 mL), then added to the aldol product solution obtained above. After antifoam AF emulsion (Dow-Corning-Nakaraitesque, diluted to a 10 percent aqueous solution, 0.4 mL) is added, the mixture is stirred with bubbling of air (1,000 mL/min). The pH is kept between 5.8–6.5 by occasional addition of Dowex® 50W-X8 ($H^+$ form, 20–50 mesh). The consumption of pyruvate may be determined by lactate dehydrogenase assay for the remaining pyruvate. The NMR spectrum of the sample taken after six hours showed a complete decomposition of pyruvate ($\delta$ 2.36 for $CH_3COCO_2^-$ and $\delta$ 1.52 for $CH_3C(OH)_2CO_2^-$ in $D_2O$).

The yeast cells are removed by centrifugation at 10,000×g (8,500 r.p.m.) for 30 minutes at 4° C. and the cells are washed twice with water (100 mL). The pH value of the combined extract is adjusted to 2.3 by addition of Dowex® 50W-X8 ($H^+$form) and the solution is concentrated in vacuo. The residue is suspended in 50 percent aqueous methanol (200 mL) and left to stand overnight (about 18 hours) at 4° C. The precipitated materials is removed by centrifugation at 10,000×g (8,500 r.p.m.) for 30 minutes at 4° C., and the residue is washed twice with 50 percent aqueous methanol (100 mL).

The solution is concentrated in vacuo and the residue is diluted with water (400 mL). The pH value is then adjusted to 5.5 by addition of concentrated aqueous ammonia solution. Alternatively, the pH value of the reaction mixture may be adjusted to 6.0 by the addition of 2N NaOH solution after the denaturation of NeuAc aldolase. To this solution is added Dowex® 1-X8 ($HCO_2^-$ form, 20–50 mesh, 100 ml of the bed volume). After washing with water, the resin is eluted with 2M formic acid (400 mL). Concentration of the eluant afforded crystalline product, which is washed successively with methanol and diethyl ether to give pure aldonic acid.

A similar result is obtained with the use of commercially available pyruvate decarboxylase (EC 4.1.1.1, Sigma P6810, $80/100 U) instead of yeast.

Sources of Aldolase

KDO aldolase (EC 4.1.2.23) was first reported by Ghalambor and Heath in 1966 as the enzyme responsible for the KDO degradation (Scheme I). After their preliminary investigation on the substrate specificity as well as the μmol scale synthesis of KDO, no synthetic application of this enzyme has been reported, while the related enzyme N-acetylneuraminic acid (sialic acid) aldolase has been extensively studied.

It is disclosed herein that the Gram-positive bacterium *Aureobacterium barkerei* strain KDO-37-2 can be induced to contain high levels of KDO aldolase. The aldolase activity from this source was assayed according to Aminoff's method (*Biochem. J.* 1961, 81, 384). Two liters of culture contained 10.2 U based on the degradation of KDO. This KDO activity is 4 times and 8 times higher than the corresponding KDO activity from *Escherichia coli* K-12 and *Aerobacter cloacae*, respectively, as reported by Gharambor (supra).

Partially purified KDO aldolase simply obtained by ammonium sulfate precipitation (8.0 U/mL; 0.19 U/mg for degradation of KDO) was used in substrate-specificity studies reported herein. The KDO aldolase employed for the kinetic analysis reported herein, was further purified via DEAE sepharose and phenyl sepharose column chromatography to a specific activity of 5.7 U/mg. The $K_m$ for D-arabinose and $V_{max}$ are 1.2M and 0.73 U/mg, respectively. The unusually high concentration of $K_m$ in the condensation compared with that in the course of degradation ($6 \times 10^{-3}$M for KDO) indicates that the enzyme may accept the open form of aldoses as acceptors in the aldol condensation. The enzymatic reaction favors the cleavage of KDO, with the equilibrium constant $K_{eq}$=[pyruvate][arabinose]/KDO $=9 \times 10^{-2}$M.

TABLE I

Relative Rates of Several Substrates for KDO Aldolase from *Aureobacterium barkerei* DKO-37-2

| substrate | relative rate[a] | substrate | relative rate[a] |
|---|---|---|---|
| D-arabinose | 100 | D-altrose | 25 |
|  | N.D.[b,c] | L-mannose | 15 |
| D-threose | 128 | L-arabinose | N.D. |
| D-erythrose | 93 | D-xylose | N.D. |
| D-ribose | 72 | D-allose | N.D. |
| 2-deoxy-D-ribose | 71 | D-glucose | N.D. |
| L-glyceraldehyde | 36 | D-mannose | N.D. |
| D-glyceraldehyde | 23 | L-fucose | N.D. |
| 2-deoxy-2-fluoro-D-arabinose | 46 | N-acetyl-D-mannosamine | N.D. |
| D-lyxose | 35 | N-acetyl-L-mannosamine | N.D. |
| 5-amido-2,5-dideoxy-D-ribose | 15 | D-fructose | N.D. |

[a]Measured at pH 7.5 with 500 mM of sugar and 10 mM of pyruvate. For detailed condition, see experimental. Specific activity based on D-arabinose is 0.2 U/mg; 1 U = 1 μmol KDO formed per min.
[b]Not detectable.
[c]Fluoropyruvate (10 mM) was used instead of pyruvate.

Scheme II (a)

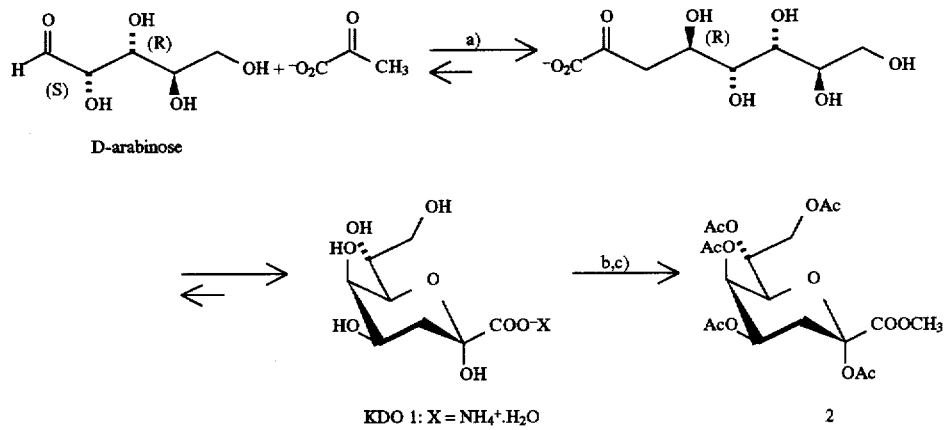

KDO 1: X = NH$_4^+$.H$_2$O    2

Scheme II (b)

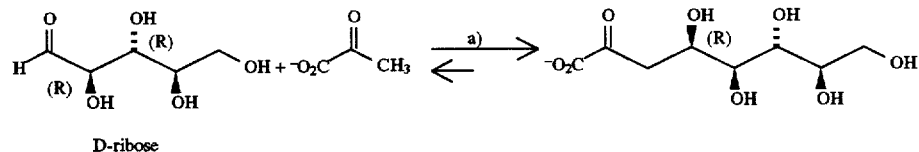

D-ribose

-continued
Scheme II (b)
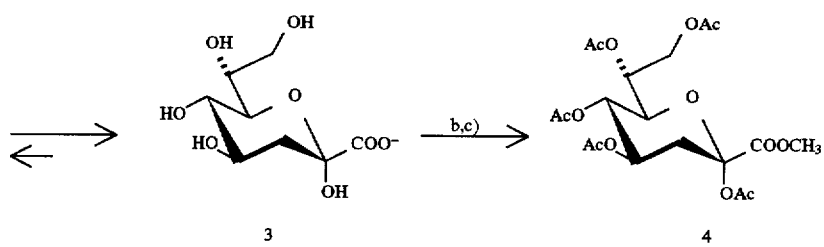
Scheme II (c)
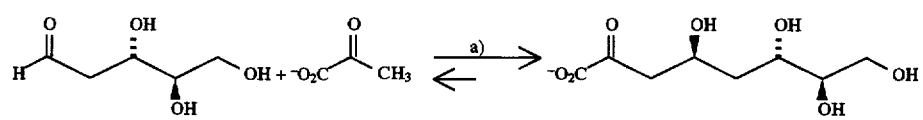
2-deoxy-D-ribose
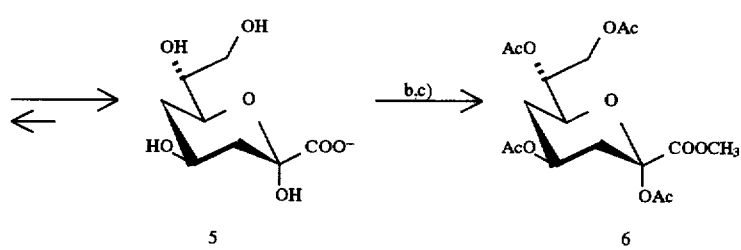
Scheme II (d)
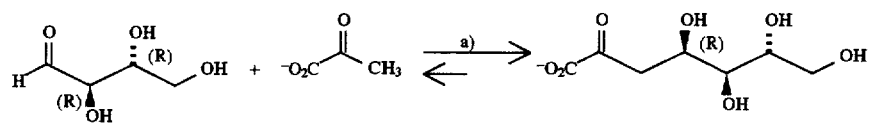
D-erythrose
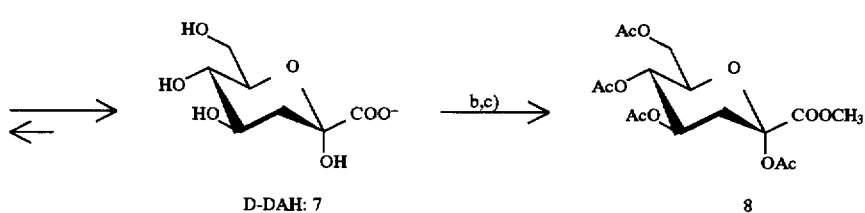
D-DAH: 7
Scheme II (e)
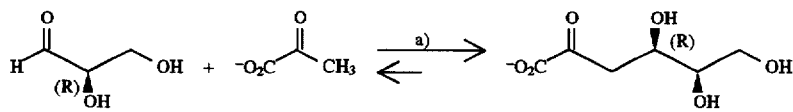
D-glyceraldehyde -continued
Scheme II (e)
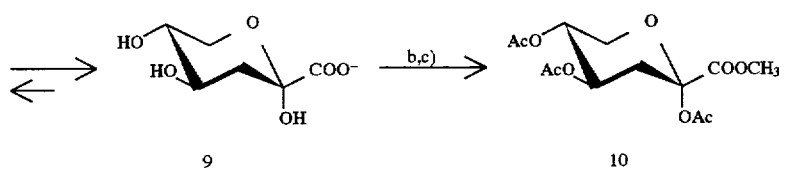
Scheme II (f)
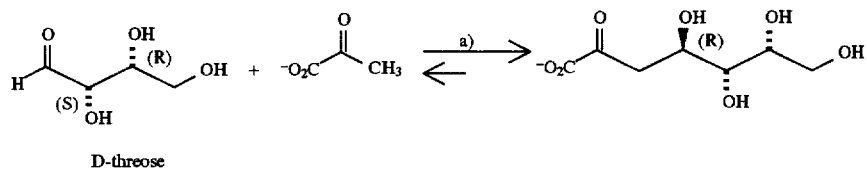
D-threose
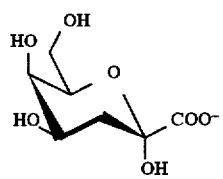
11
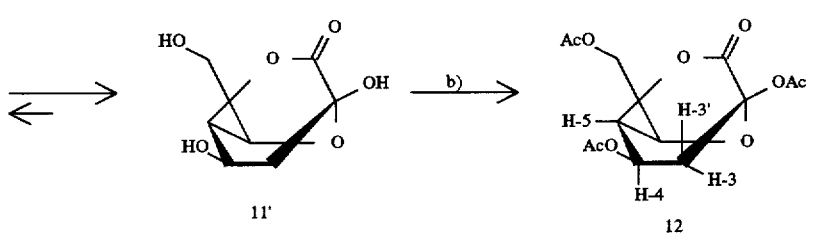
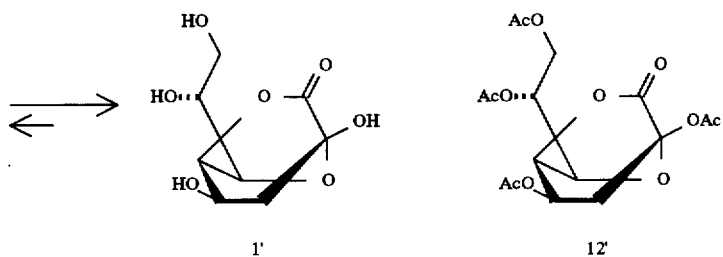
Scheme II (g)
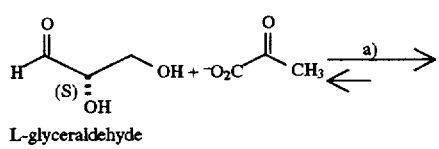
L-glyceraldehyde
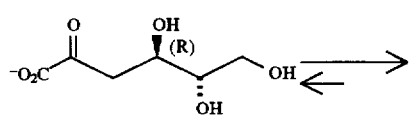
-continued
Scheme II (g)
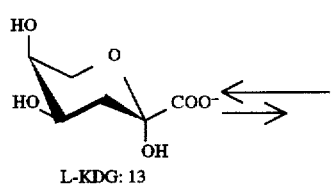
L-KDG: 13

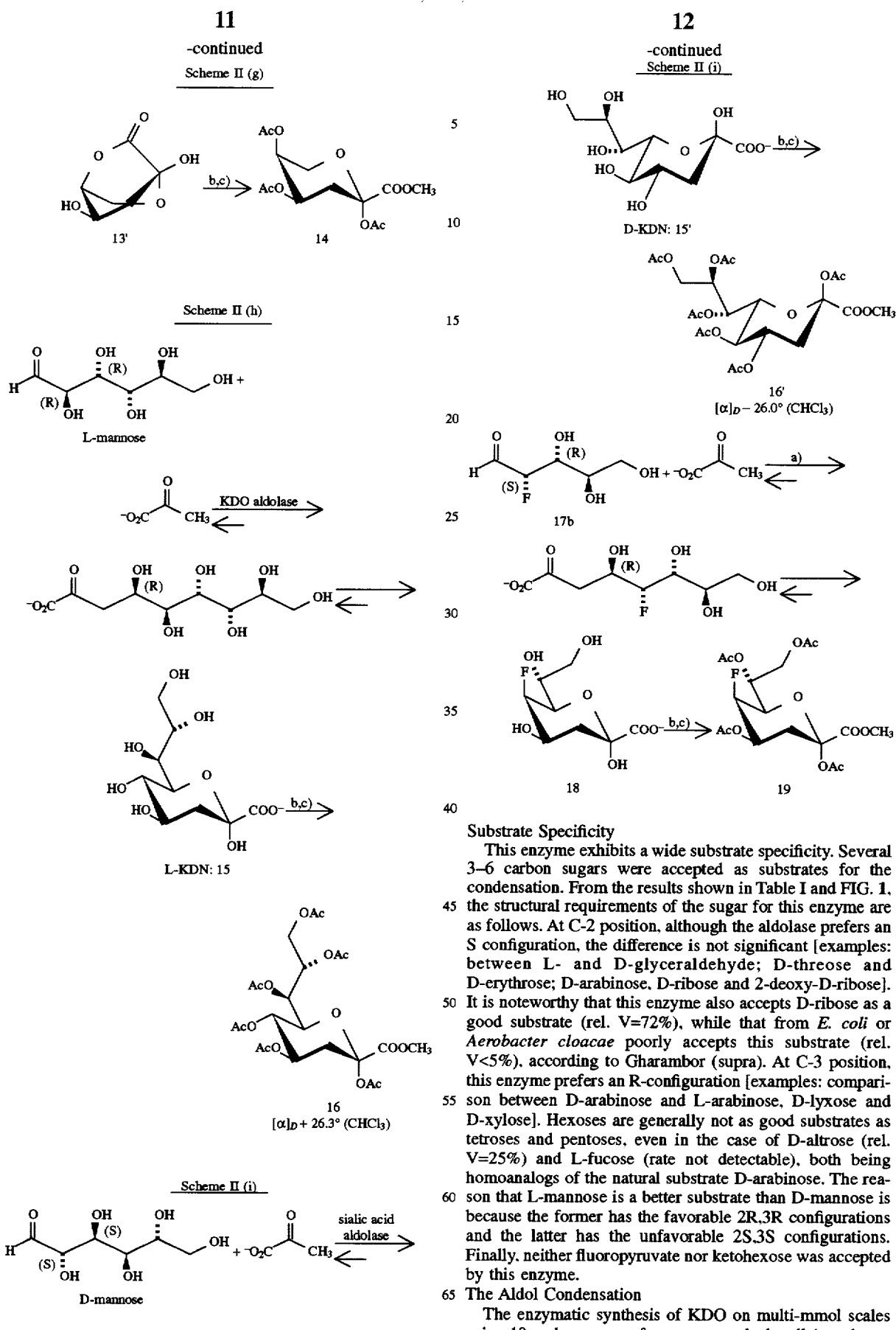

Substrate Specificity

This enzyme exhibits a wide substrate specificity. Several 3–6 carbon sugars were accepted as substrates for the condensation. From the results shown in Table I and FIG. 1, the structural requirements of the sugar for this enzyme are as follows. At C-2 position, although the aldolase prefers an S configuration, the difference is not significant [examples: between L- and D-glyceraldehyde; D-threose and D-erythrose; D-arabinose, D-ribose and 2-deoxy-D-ribose]. It is noteworthy that this enzyme also accepts D-ribose as a good substrate (rel. V=72%), while that from *E. coli* or *Aerobacter cloacae* poorly accepts this substrate (rel. V<5%), according to Gharambor (supra). At C-3 position, this enzyme prefers an R-configuration [examples: comparison between D-arabinose and L-arabinose, D-lyxose and D-xylose]. Hexoses are generally not as good substrates as tetroses and pentoses, even in the case of D-altrose (rel. V=25%) and L-fucose (rate not detectable), both being homoanalogs of the natural substrate D-arabinose. The reason that L-mannose is a better substrate than D-mannose is because the former has the favorable 2R,3R configurations and the latter has the unfavorable 2S,3S configurations. Finally, neither fluoropyruvate nor ketohexose was accepted by this enzyme.

The Aldol Condensation

The enzymatic synthesis of KDO on multi-mmol scales using 10 molar excess of pyruvate worked well (e.g. 1 was obtained in 67% yield). The synthetic route is illustrated in Scheme II (a). The reagents employed in this synthesis are as follows:

| Step | Reagent or Enzyme |
|------|-------------------|
| (a)  | KDO aldolase      |
| (b)  | Ac$_2$O/py,DMAP   |
| (c)  | CH$_2$N$_2$.      |

The yield of the enzymatic reaction is comparable to the highest one obtained by the modified Cornforth synthesis (66%). The crystalline KDO ammonium salt monohydrate was isolated in 37% yield: $[\alpha]^{26}$ D +40.3° (c 2.06, H$_2$O) [lit. according to Unger: $[\alpha]^{27}$D +42.3° (c, 1.7, H$_2$O), authentic sample from Sigma $[\alpha]^{26}$D +40.2° (c 2.06, H$_2$O)]. (Unger: Adv. Carbohydr. Chem. Biochem. 1981, 38, 323.) The $^1$H NMR spectrum in D$_2$O is identical with that of an authentic sample, although it is complicated by the fact that KDO exists as an anomeric mixture of pyranose and furanose forms, and readily cyclizes to the corresponding lactone in aqueous solution. The crystalline ammonium salt was further converted to pentaacetate methyl ester derivative 2, whose $^1$H NMR spectrum was in good accordance with that reported previously and clearly shows the $^5C_2$-pyranose conformation (Table II).

Several substrates with good or fair relative rate are shown to be employable in the aldol condensation. The reactions with D-ribose and 2-deoxy-D-ribose are illustrated in Schemes II (b) and (c) respectively. These reactions took place smoothly to give 3 (57% after derivation to 4) and 5 (47% as 6), respectively. $^1$H NMR spectra of 3, 4, 5, and 6 clearly show a $^5C_2$ pyranose form in both products (Table III). The $^1$H spectrum of 6 is shown in FIG. 2. It is noteworthy that in these cases, even though the relative rates are lower (72% for D-ribose and 71% for 2-deoxy-D-ribose) than that of D-arabinose, TLC analysis of the reaction products showed no starting material left, whereas a substantial amount of starting material always remains in the reaction with D-arabinose. It is suggested that formation of the pyranose form of 3 and 5, where all substituents are located in the stable orientation, further shifted the equilibrium toward condensation.

TABLE II $^1$H NMR Analysis of Pyranose, Furanose and 1 → 5 Lactone Forms Observed in the Products Possessing C-5 Axial Substituent in the Pyranose Form α-pyranose form:
X = OH or OAc β-pyranose form:
X = OH furanose form:
Y = H-3 and H-3' lactose form:
X = OH or OAc

| compound | chemical shifts (δ, ppm) | | coupling constants (Hz) | | | |
|----------|------|------|------|------|------|------|
|          | H-3  | H-3' | $J_{3,3'}$ | $J_{3,4}$ | $J_{3',4}$ | $J_{3,5}$ |
| 1 (KDO, in D$_2$O) | | | | | | |
| α-pyranose form | 1.863 | 1.951 | 13.0 | 5.5 | 12.0 | 1.0 |
| β-pyranose form | 2.373 | 1.735 | 11.7 | 5.0 | 11.7 | 1.0 |
| furanose form* | 2.275 | 2.351 | 13.5 | 7.5 | 7.5 | — |
| 1' (in D$_2$O) | 2.053 | 2.562 | 14.0 | 3.0 | 7.5 | — |
| 2 (in CDCl$_3$) | 2.245 | 2.201 | 13.0 | 6.0 | 12.0 | — |
| 11 (in D$_2$O) | | | | | | |
| α-pyranose form | 1.90–1.98 | | — | — | — | — |
| furanose form | 2.301 | 2.384 | 13.4 | 7.0 | 7.0 | — |
| 11' (in D$_2$O) | 2.072 | 2.576 | 14.2 | 3.1 | 7.3 | — |
| 12 (in CDCl$_3$) | 2.339 | 2.972 | 14.9 | 2.4 | 9.5 | 0.6 |
| 12' (in CDCl$_3$)$^b$ | 2.10 | 2.80 | 15.0 | 2.5 | 9.0 | — |
| 13 (in D$_2$O) | | | | | | |
| α-pyranose form | 1.873 | 1.984 | 13.0 | 5.2 | 11.9 | — |
| furanose form | 2.284 | 2.341 | 13.1 | 6.4 | 6.4 | — |
| 13' (in D$_2$O) | 2.051 | 2.521 | 14.1 | 3.2 | 7.5 | — |
| 14 (in CDCl$_3$) | 2.292 | 2.288 | — | 7.0 | 10.1 | 0.4 |

TABLE III $^1$H NMR Analysis of the α-Pyranose Form Observed in the Products Possessing C-5 Equatorial Substituent α-pyranose form:
X = OH or OAc; Y = OH, OAc or H

| compound | chemical shifts (δ, ppm) | | coupling constants (Hz) | | | |
|----------|------|------|------|------|------|------|
|          | H-3 eq | H-3 ax | $J_{3\,eq,3\,ax}$ | $J_{3\,eq,4}$ | $J_{3\,ax,4}$ | $J_{3\,eq,5\,eq}$ |
| 3$^a$  | 2.148 | 1.773 | 13.0 | 5.1 | 11.4 | — |
| 4$^b$  | 2.559 | 2.010 | 13.5 | 5.2 | 11.6 | — |
| 5$^a$  | 2.094 | 1.591 | 12.7 | 4.6 | 12.1 | 1.8 |
| 6$^b$  | 2.454 | 1.783 | 13.1 | 4.8 | 11.6 | 1.8 |
| 7$^a$  | 2.180 | 1.773 | 13.0 | 5.1 | 11.8 | — |
| 8$^b$  | 2.658 | 2.087 | 13.6 | 5.2 | 11.4 | — |
| 9$^a$  | 2.176 | 1.795 | 13.1 | 5.1 | 11.6 | — |
| 10$^b$ | 2.618 | 1.948 | 13.5 | 5.2 | 11.2 | — |

$^a$Measured in D$_2$O.
$^b$Measured in CDCl$_3$.

The products 7 (3-deoxy-D-arabino-2-heptulosonic acid, DAH, 39% as 8) and 9 (11% as 10) were also obtained from D-erythrose and D-glyceraldehyde, as illustrated in Schemes II (d) and (e) respectively. These yields indicate that this aldolase-catalyzed condensation is also useful for the synthesis of lower homologs of KDO. The phosphate of 7 (DAHP) plays an important role in the shikimate synthesis pathway in plants and microorganisms. The selected chemical shifts and coupling constants for the $^1$H NMR spectra of products 3–10 are summarized in Table III.

Scheme II (f) illustrates the aldolase catalyzed condensation reaction can be employed to produce product 11 from D-threose. Product 11 has a $^1$H NMR spectrum similar to that of KDO. The reaction with L-glyceraldehyde, illustrated in Scheme II (g) afforded 13 (2-keto-3-deoxy-L-gluconic acid, KDG), an enantiomer of D-KDG, whose phosphate (KDGP) is an intermediate in the Entner-Doudoroff pathway. (Entner, N.; Doudoroff, M. J. *Biol. Chem.* 1952, 196, 853.) The $^1$H NMR spectrum of 13 was very complicated (see experimental). To clarify the stereochemistry, preparation of derivatives was attempted; however, the products were still difficult to identify. The only isolable component from 11 was a bicyclic lactone. The structure was determined as 12 (Scheme II) by comparing its $^1$H NMR spectrum with that of the higher homolog 12', which had been obtained from KDO and unambiguously characterized previously. (Charon, D.; Auzanneau, F.-I.; Mérienne, C.; Szabó, L. *Tetrahedron Lett.* 1987, 23, 1393.)

In its $^1$H NMR spectrum (Table II), a long range coupling between H-3 and H-5 (0.6 Hz) indicates that the pyranose form of the product exists as a twisted boat conformation, and all of the coupling constants are consistent with those observed in the case of 12'. It is interesting that in the spectra of 11, 13 and KDO, a substantial proportion of the similar signals were observed, where one of the H-3 signal appears at very low field (Table II). From these results, it is assumed that the bicyclic 1<<5 lactones 1', 11'and 13' form at nearly neutral pH. The formation of 1<<7 lactone is excluded, since those signals were observed in the case of a hexulosonate 13'without any C-7 hydroxy group. The homologs prepared here also proceed through a spontaneous 1<<5 lactone formation, as already proposed previously for KDO. (Menton, L. D., et al. *Carbohydr. Res.* 1980, 80, 295.) Compound 13 mainly exists as $^5$C$_2$ pyranose form as indicated in 14.

The reaction with L-mannose illustrated in Scheme II (h) gave 15 (3-deoxy-L-glycero-L-galacto-2-nonulosonic acid, L-KDN, 61% as 16), which is an enantiomer of D-KDN, a component in polysialoglycoprotein and ganglioside of rainbow trout eggs. (Lin, C.-H., et al., *J. Am. Chem. Soc.*, in press; Nadano, D. et al. *J. Biol. Chem.* 1986, 261, 11550; and Song, Y., et al. *J. Biol. Chem.* 1991, 266, 21929.) The optical rotation [[α]$^{25}$D +26.3° (CHCl$_3$)] and $^1$H NMR spectrum of 16 were in good accordance with those of 16'[[α]$^{25}$D–26.0° (CHCl$_3$)], which was obtained via reaction with D-mannose catalyzed by sialic acid aldolase, as illustrated in Scheme II (i), except for the sign of rotation (Tetrahedron 1990, 46, 201). The availability of both enantiomers of KDN may develop new analogs of sialyl oligosaccharides. (Ichikawa, Y., et al. *Anal. Biochem.* 1992, 202, 215.)

Finally, the aldol reaction with an unnatural sugar containing a fluorine atom was conducted to give 18 (19% of 19). By comparing the $^1$H NMR spectra, the proportion of the β-isomer (10.71) of 18 was ca. 1.5 times higher than that of KDO (6.9%), probably due to the absence of furanose and 1<<5 lactone forms. This result suggests that 18 might be a good substrate for CMP-KDO synthetase, since the enzyme accepts the unstable β-form of KDO as a substrate. (Kohlbrenner, W. E. and Fesik, S. W., *J. Biol. Chem.* 1985, 260, 14695.) We therefore synthesized 18 in a larger scale by combining the use of KDO aldolase and pyruvate decarboxylase, which made the workup procedure much easier. Preliminary study using 18 toward CMP-KDO synthetase which had recently been cloned and over-expressed in this group showed that 18 was accepted to the enzyme.

Based on these results, the stereochemical course of the aldol condensation catalyzed by this KDO aldolase is probably as follows: The attack of pyruvate always takes place on the re face of the carbonyl group of the substrates, a facial selection complementary to sialic acid aldolase reactions (si face attack). The stereochemical requirements of substrates and the stereochemical course of the aldol condensation are indicated in FIG. 3. It is concluded that in general the enzyme accepts substrates with an R-configuration at C-3. The substrates with an S configuration at C-2 is kinetically favored, while those with R configuration at C-2 are thermodynamically favored to give a better yield.

Synthesis of Decarboxylated Analogs

Decarboxylation of KDO and its analogs will yield the corresponding aldose derivatives. A synthetic route employing decarboxylation of KDO aldolase condensation products is illustrated in Schemes III (a) and (b). The reagents employed in these synthetic routes is as follows:

| Step | Reagent |
| --- | --- |
| (a) | Ac$_2$, DMAP/pyridine |
| (b) | CsCO$_3$, BnBr/DMF |
| (c) | H$_2$,Pd—C/EtOH |
| (d) | (COCl)$_2$/toluene |
| (e) | 17, DMAP/pyridine-toluene |
| (f) | t-BuSH, hv |
| (g) | Me$_3$N=C=NEt (WSCI)—Cl, 17 (5 eq.), T-CUSH, DMAP, Et$_3$N, MS4A/Ch$_2$Cl$_2$, hv |

The aldodeoxyheptose structure is particularly interesting since a number of heptoses are widely distributed in nature, some of which play important roles in metabolic pathways. Barton's radical-mediated decarboxylation of the penta-O-acetyl derivative 20a obtained from the corresponding benzyl ester 20b seems to be the most straightforward route to the desired heptose derivative 21. (e.g., Crich, D. and Lim, L. B. L. *J. Chem. Soc. Perkin I* 1991, 2209 and Auzanneau, F.-I. et al. *Carbohydr. Res.* 1990, 201, 337.)

There have recently been growing interests in the synthesis of physiologically active carbohydrate- and nucleic acid-related compounds via anomeric radical intermediates. It appears to us that radical-mediated reaction stabilized both electron withdrawing and donating group (capto-dative effect), e.g. Viehe, H. G. et al. *Acc. Chem. Res.* 1985, 18, 148.) at anomeric position [—C(•)(OAc)O-type] is rare (only a few related examples [eg.

Scheme III (a)
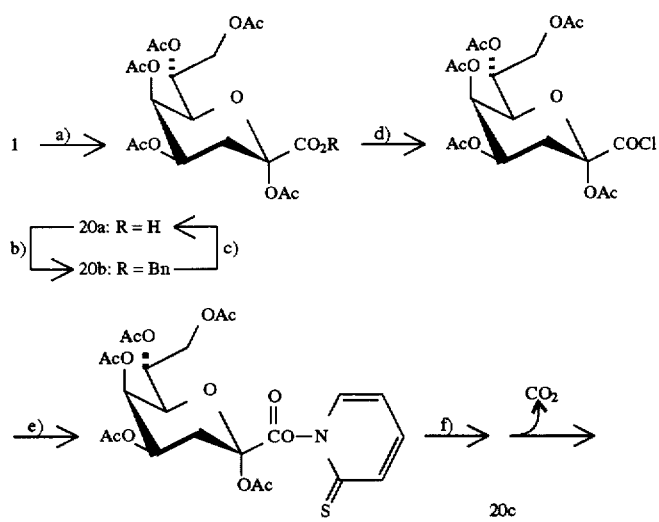
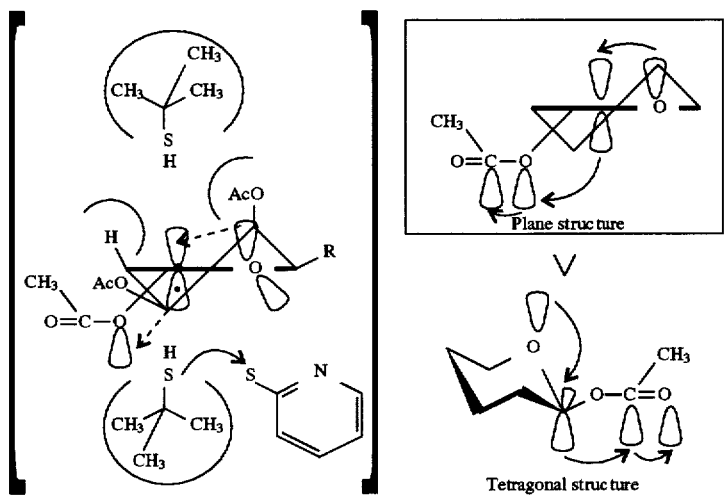
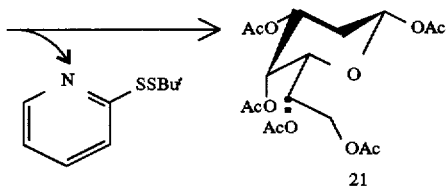
Scheme III (b)
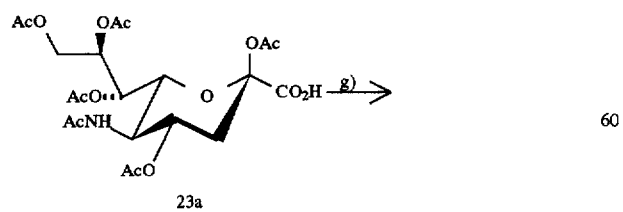

-continued
Scheme III (b)

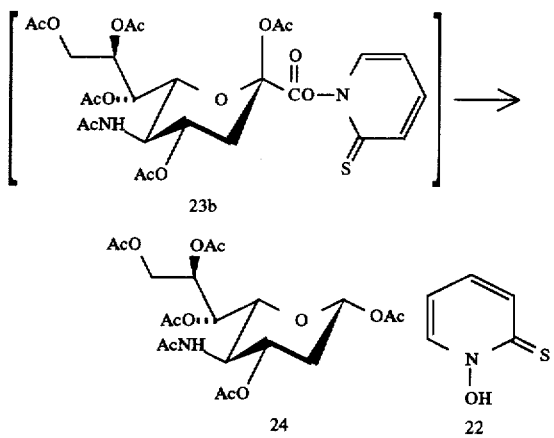

—C(•)(CO₂Me)O— type, —C(•)(CHF₂)O— type] are known), while examples in the case of simple anomeric radical [—C(•)(H or R)O— type] and the one bearing two electron donating oxygen atom [—C(•)(OR))-type] have been extensively studied. (e.g. Crich, D. and Lim, L. B. L. *J. Chem. Soc. Perkin I* 1991, 2205 and *J. Chem. Soc. Perkin I* 1991, 2209; Schmidt, R. et al. *Tetrahedron Lett.* 1988, 29, 3643; Myrvold, S. et al. *J. Am. Chem. Soc.* 1989, 111, 1861; Motherwell, W.B. et al. *Synlett.* 1989, 68; and Samadi, M. *J. Med. Chem.* 1992, 35, 63.) The radical intermediate was formed by the thermal decomposition of the thiohydroxamate 20c generated in situ from the corresponding acid chloride and 22 in the presence of azobisisobutyronitrile (AIBN). The subsequent trapping with tributyltin hydride resulted in only a disappointing (less than 2%) yield of 21. The yield was, however, dramatically improved to 68% by irradiation with white light in the presence of t-butylmercaptane.

The $^1$H NMR spectrum of 21 clearly shows the exclusive β-anomer (δ 5.75, dd, $J_{1,2eq}$=3.0, $J_{1,2ax}$=10.0 Hz, H-1), indicating that the abstraction of hydrogen atom from t-butylmercaptane took place at the bottom side of the six-membered ring. The proposed mechanism for the exclusive formation of β-isomer is as follows. The stable conformer of the radical intermediate which is stabilized both by the electron-donating and withdrawing effects is supposed to be in a plane form as depicted in Scheme III, which allows the maximum interaction between the one-electron p orbital and the lone pair electrons on the adjacent ring oxygen. t-Butylmercaptane is easily accessible from the bottom side, while the approach from the top side is sterically hindered by the hydrogen and acetoxy groups. This explanation in terms of kinetic control is well matched with the thermodynamic stability of the β-product.

The radical process was also applied to the synthesis of the decarboxylated analog of N-acetylneuraminic acid. It turned out, however, that all attempts for the synthesis of the acyl chloride resulted in a complex mixture, even from fully protected peracetate form 23a of sialic acid, because NHAc proton still has a substantial reactivity to chlorinating reagents. The direct formation of thiohydroxamate 23b was also found to be difficult because of the inherent steric hindrance around carbonyl group in the starting material. Through an extensive examination of the reaction conditions, it was found that the combination of ethyl (diethylamino)propylcarbodiimide hydrochloride (WSCI-13 Cl, 1.5 eq) and excess of 22 (5.0 eq) worked well for the in situ formation and degradation of thiohydroxamate, to give 24 (27% yield from 23a). This condition has the advantage that the reaction can be carried out in one step. The newly formed product was exclusively an α-anomer where the OAc group is located in the equatorial orientation, consistent with the result obtained in the decarboxylation of KDO derivative. (Haverkamp, J. et al. *Eur. J. Biochem.* 1982, 122, 305.)

Preparation of Examples

General

Optical rotations were measured on Perkin-Elmer 241 spectrophotometer. UV and visible spectra were recorded on a Beckmann DU-70 spectrometer. $^1$H and $^{13}$C NMR spectra were recorded at 400 and 500 MHz on Bruker AMX-400 and AMX-500 spectrometer. High-resolution mass spectra (HRMS) were recorded on a VG ZAB-ZSE mass spectrometer under fast atom bombardment (FAB) conditions. Column chromatography was carried out with silica gel of 70–230 mesh. Preparative TLC was carried out on Merck Art. 5744 (0.5 mm).

Isolation of the Microorganism

*Aureobacterium barkerei* containing high levels of KDO aldolases was selected with the S medium containing 0.25% of synthetic KDO mixture as carbon source (20 mL) in serum bottles (158 mL) and incubated at 37° C. for 2 days with shaking (250 r.p.m.). (McNicholas, P. A. et al. *Carbohydr. Res.* 1986, 146, 219 and Shirai, R.; and Ogura, H. *Tetrahedron Lett.* 1989, 30, 2263.) The bottles which showed turbidity were transferred to the same fresh medium. After several transfers, the cultures were plated on the S medium agar plates (1.5% agar) containing 0.25% of synthetic KDO mixture. The isolated colonies were transferred to the liquid medium as described above. To confirm the utilization of KDO, the disappearance in the medium was monitored by TLC as described in the synthesis of KDO. The cultures which showed the utilization of KDO were harvested by centrifugation and resuspended in 50 nM phosphate buffer (pH 7.0). The cell suspension was incubated with 1% (w/v) of authentic KDO (from Sigma) at 37° C. overnight to confirm the degradation of KDO by TLC. The cultures were then replated on LB agar plates to ensure the purity of the culture.

Preparation of the Enzyme

With one slight modification, the incubation was carried out according to the procedure reported by Gharambor (supra). The ingredients of the medium were as follows: NH₄Cl (5 g), K₂SO₄ (1 g), MgSO₄.7H₂O (200 mg), CaCl₂ (20 mg), FeSO₄.7H₂O (1 mg), yeast extract (1 g), Na₂HPO₄.7H₂O (10 g), and KH₂PO₄ (3 g) in distilled water (1 L), at pH 7.2. To a 50 mL of this medium in a 100 mL Erlenmeyer flask, were added D-glucose (40% solution in water, 25 μL) and KDO (100 mg, 0.2%), and a loopful of *Aureobacterium barkerei* KDO-37-2 was incolutated. The flask was shaken at 250 r.p.m. on a gyrorotary shaker at 30° C. for 16 h. The seed culture thus obtained was poured into the 1950 mL of the same incubation medium containing KDO (3.9 g). The mixture was divided and poured into two of 2.8 L Erlenmeyer flasks. The flasks were shaken at 250 r.p.m. at 30° C. for 24 h. The growth of microorganism was estimated by OD at 600 nm to be 1.90. The cells were harvested at 10,000×g for 30 min at 4° C. and washed with 50 mM potassium-sodium phosphate buffer (pH 7.5). The collected cells were then resuspended in the same buffer solution (20 mL) and disrupted by French-pressure apparatus (at 16,000 lb/in). The cell debris were removed by centrifuge at 23,000×g for 1 h at 4° C. to give the supernatant (ca. 20 mL) as the crude enzyme preparation. The enzyme activity was determined to be 1.45 U/mL for the degradation of KDO according to the method of Aminoff (*Biochem. J.* 1961, 81, 384). Ammonium sulfate precipitation between 45–75% saturation was collected and dialyzed in phosphate buffer (2 L; 100 mM, 1 mM of dithiothreitol, 2 L) to give partially purified enzyme (13.5 mL, 1.73 U/mL for KDO degradation), according to the method of Kim (*J. Am. Chem. Soc.* 1988, 110, 6481).

Kinetic Measurements

The rates for aldolase-catalyzed reactions were obtained by measuring the amount of remaining pyruvate, according the method of Kim (supra). The reactions were carried out in 0.1M phosphate buffer (pH 7.5) containing: varied concentrations of pyruvate, 2.0, 3.33, 5, and 10 mM; varied concentrations of D-arabinose, 0.2, 0.25, 0.33, and 0.50M in 0.5 mL of solution. Each solution was incubated at 37° C. Periodically, a small aliquot (25–100 μL) was withdrawn and mixed with an assay solution (1.4 mL) containing 0.1M phosphate (pH 7.5) buffer, 0.3 mM NADH, and 20–30 U of L-lactate dehydrogenase. The decrease in absorbance at 340 nm was measured and converted into the amount of the unreacted pyruvate using 6220 $M^{-1}cm^{-1}$ for the molecular absorbance of NADH. The kinetic parameters were obtained from the Lineweaver-Burk plots.

For the relative rate measurements, the concentration of pyruvate (fluoropyruvate) and sugar were fixed at 10 mM and 0.5M, respectively. Other conditions were the same as above.

EXAMPLES

The following Examples illustrate particular embodiments of the present invention and are not limiting of the specification and claims in any way.

Example 1

Ammonium 3-deoxy-α-D-manno-2-octulosonate monohydrate (KDO ammonium salt monohydrate, 1).

D-Arabinose (250 mg, 1.67 mmol), sodium pyruvate (1.83 g, 16.7 mmol), dithiothreitol (1.5 mg), $NaN_3$ (2% solution in water, 100 μL), $NaHPO_4 \cdot 7H_2O$ (53 mg), and $KH_2PO_4$ (13 mg) were added to the KDO aldolase (5.1 U, 10 mL). The pH was adjusted to 7.5 and the mixture was stirred under $N_2$ at 30° C. for 3 days. The product was purified by treatment with a Dowex-1 resin column (bicarbonate form) eluted with a linear gradient from 0 to 0.25M of ammonium bicarbonate. KDO ammonium salt was further purified by Biogel P-2 column. The fraction eluted with $H_2O$ containing KDO was collected and its total amount was estimated to be 1.11 mmol (67%) by Aminoff's assay (supra). The residue after lyophilization was recrystallized from aqueous ethanol to give colorless plates (168 mg, 37% from D-arabinose): mp 123–125° C. (decomposition) [lit. according to Hershberger: mp 121–123° C., authentic sample from Sigma mp 123–125° C. (decomposition)]; $[\alpha]^{26}D$ +40.3° (c 2.06, water) [lit. according to Hershberger: $[\alpha]^{27}D$ +42.3° (c 1.7, water), authentic sample from Sigma $[\alpha]^{26}D$ +40.2° (c 2.03, water)]. Its $^1H$ NMR spectrum in $D_2O$ was identical with that of an authentic sample. (Hershberger: *J. Biol. Chem.* 1968, 243, 1585.) A small portion was converted to pentaacetate methyl ester derivative 2: $^1H$ NMR ($CDCl_3$) δ 1.994 (3H, s, acetyl), 1.998 (3H, s, acetyl), 2.045 (3H, s acetyl), 2.108 (3H, s, acetyl), 2.139 (3H, s, acetyl), 2.201 (1H, dd, $J_{3ax,4}$=12.0, $J_{3ax,3eq}$=13.0 Hz, H-3ax), 2.245 (1H, dd, $J_{3eq,4}$=6.0, $J_{3eq,3ax}$=13 Hz, H-3eq), 3.810 (3H, s, $COOCH_3$), 4.113 (1H, dd, $J_{8',7}$=12.5, $J_{8',8}$=12.5 Hz, H-8'), 4.173 (1H, dd, $J_{6,5}$=1.3, $J_{6,7}$=9.5 Hz, H-6), 4.475 (1H, dd, $J_{8,7}$=4.0, $J_{8,8'}$=12.5 Hz, H-8), 5.220 (1H, ddd, $J_{7,8}$=4.0, $J_{7,6}$=9.5, $J_{7,8'}$=12.5 Hz, H-7), 5.322 (1H, ddd, $J_{4,5}$=3.0, $J_{4,3eq}$=6.0, $J_{4,3eq}$=6.0, $J_{4,3ax}$=12.0 Hz, H-4), 5.385 (1H, dd, $J_{5,6}$=1.3, $J_{5,4}$32 3.0Hz, H-5). $^1H$ NMR spectrum was in good accordance with that reported previously by Unger (*Adv. Carbohydr. Chem. Biochem.* 1981, 38, 323).

Example 2

Methyl 2,4,5,7,8-penta-O-acetyl-3-deoxy-α-D-altro-2-octulosonate (4).

In the same manner as described for the preparation of 1, the product 3 (as ammonium salt) was prepared from D-ribose (0.33 mmol): $^1H$ NMR ($D_2O$) δ 1.773 (1H, dd, $J_{3ax,4}$=11.9, $J_{3ax,3eq}$=13.0 Hz, H-3ax), 2.148 (1H, dd, $J_{3eq,4}$=5.1, $J_{3eq,3ax}$=13.0 Hz, H-3eq), 3.500 (1H, dd, $J_{5,4}$=9, $J_{5,6}$=10.0 Hz, H-5), 3.745 (1H, dd, $J_{8,7}$=7.3, $J_{8,8'}$=12.1 Hz, H-8), 3.789 (1H, dd, $J_{8',7}$=3.7, $J_{8',8}$=12.1 Hz, H-8'), 3.809 (1H, dd, $J_{6,7}$=2.8, $J_{6,5}$=10.0 Hz, H-6), 3.901 (1H, ddd, $J_{4,3eq}$=5.1, $J_{4,5}$=9.1, $J_{4,3ax}$=11.9 Ha, H-4), 4.004 (1H, dd, $J_{7,6}$=2.8, $J_{7,8}$=3.7, $J_{7,8'}$=7.3 Hz, H-7). This was converted to 4 by the successive treatment with acetic anhydride-pyridine-DMAP (see also the preparation of 20b) and etherial diazomethane solution. The product was purified with silica gel preparative TLC to afford 4 (87.7 mg, 57% from D-ribose) as an oil, $[\alpha]^{25}D$ +70.9° (c 0.81, $CHCl_3$); $^1H$ NMR ($CDCl_3$) δ 2.010 (1H, dd, $J_{3ax,4}$=11.6, $J_{3ax,3eq}$=13.5 Hz, H-3ax), 2.030 (3H, acetyl), 2.050 (3H, s, acetyl), 2.064 (3H, s, acetyl), 2.105 (3H, s, acetyl), 2.154 (3H, s, acetyl), 2.559 (1H, dd, $J_{3eq,4}$=5.2, $J_{3eq,3ax}$=13.5 Hz, H-3eq), 3.793 (3H, s, $COOCH_3$), 4.084 (1H, dd, $J_{6,7}$=3.2, $J_{6,5}$=10.3 Hz, H-6), 4.241 (1H, dd, $J_{8,7}$=7.0, $J_{8,8'}$=12.0 Hz, H-8), 4.415 (1H, dd, $J_{8',7}$=4.0 $J_{8',8}$=12.0 Hz, H-8'), 5.110 (1H, dd, $J_{5,4}$=9.3, $J_{5,6}$=10.3 Hz, H-5), 5.169 (1H, ddd, $J_{7,6}$=3.2, $J_{7,8}$4.0, $J_{7,8'}$=7.0 Hz, H-7), 5.271 (1H, ddd, $J_{4,3eq}$=5.2, $J_{4,5}$=9.3, $J_{4,3ax}$=11.6 Hz, H-4); $^{13}C$ NMR ($CDCl_3$) δ 20.52, 20.56, 20.56, 20.67, 20.67, 35.47, 53.12, 61.23, 68.33, 68.96, 69.85, 71.98, 96.66, 166.21, 167.94, 169.52, 169.85, 169.89, 170.38. HRMS (M+$Cs^+$) calcd $C_{19}H_{26}O_{13}Cs$ 595.0428, found 595.0428.

Example 3

Methyl 2,4,7,8-tetra-O-acetyl-3,5-dideoxy-α-D-manno-2-octulosonate (6).

In the same manner as 3, the product 5 (as ammonium salt) was prepared from 2-deoxy-D-ribose (0.33 mmol): $^1H$ NMR ($D_2O$) δ 1.400 (1H, ddd, $J_{5ax,4}$=11.9, $J_{5ax,6}$=11.9, $J_{5ax,5eq}$=12.3 Hz, H-5ax), 1.591(1H, dd, $J_{3ax,4}$=12.1, $J_{3ax,3eq}$=12.7 Hz, H-3ax), 2.009 (1H, dddd, $J_{5eq,3}$=1.8, $J_{5eq,6}$=2.2, $J_{5eq,4}$=4.6, $J_{5eq,5ax}$=12.3 Hz, H-5eq), 2.094 (1H, ddd, $J_{3eq,5eq}$=1.8, $J_{3eq,4}$=4.6, $J_{3eq,3ax}$=12.7 Hz, H-3eq), 3.398 (1H, dddd, $J_{8,7}$=7.1, $J_{8,8'}$=11.8 Hz, H-8), 3.588 (1H, dd, $J_{8',7}$=4.1, $J_{8',8}$=11.8 Hz, H-8'), 3.786 (1H, ddd, $J_{7,8}$=4.1, $J_{7,6}$=4.6, $J_{7,8}$=7.1 H8, H-7), 3.945 (1H, ddd, $J_{6,5eq}$=2.2, $J_{6,7}$=4.6, $J_{6,5ax}$=11.9 Hz, H-6), 4.112 (1H, dddd, $J_{4,3eq}$=4.6, $J_{4,5eq}$=4.6, $J_{4,5ax}$=11.9, $J_{4,3ax}$=12.1 Hz, H-4). This was converted to 6 (62.2 mg, 47% from 2-deoxy-D-ribose): $[\alpha]^{25}D$ +86.0° (c 0.56, $CHCl_3$); $^1H$ NMR ($CDCl_3$) δ 1.488 (1H, ddd, $J_{5ax,4}$=12.0, $J_{5ax,6}$=12.0, $J_{5ax,5eq}$=12.7 Hz, H-5ax), 1.783 (1H, dd, $J_{3ax,4}$=11.6, $J_{3ax,3eq}$=13.1 Hz, H-3ax), 2.045 (3H, s, acetyl), 2.054 (3H, s, acetyl), 2.070 (3H, s, acetyl), 2.123 (3H, s, acetyl), 2.177 (1H, dddd, $J_{5eq,3eq}$=1.8, $J_{5eq,6}$=2.2, $J_{5eq,4}$=4.7, $J_{5eq,5ax}$=12.7 Hz, H-5eq), 2.454 (1H, ddd, $J_{3eq,5eq}$=1.8, $J_{3eq,4}$=4.8, $J_{3eq,3ax}$=13.1 Hz, H-3eq), 3.782 (3H, s, $COOCH_3$), 4.034 (1H, ddd, $J_{6,5eq}$=2.2, $J_{6,7}$=7.6, $J_{6,5ax}$=12.0 Hz, H-6), 4.169 (1H, dd, $J_{8,7}$=5.1, $J_{8,8'}$=12.2 Hz, H-8), 4.457 (1H, dd, $J_{8',7}$=2.8, $J_{8',8}$=12.2 Hz, H-8'), 5.093 (1H, ddd, $J_{7,8}$=2.8, $J_{7,8'}$=5.1, $J_{7,6}$=7.6 Hz, H-7), 5.186 (1H, dddd, $J_{4,5eq}$=4.7, $J_{4,3eq}$=4.8, $J_{4,3ax}$=11.6, $J_{4,5ax}$=12.0 Hz, H-4); $^{13}C$ NMR (CDCl$_3$) δ 20.56, 20.56, 20.73, 20.96, 32.21, 36.03, 52.96, 61.82, 65.72, 69.00, 71.96, 97.61, 167.02, 167.96, 169.81, 170.06, 170.32. HRMS (M+Cs$^+$) calcd C$_{17}$H$_{24}$O$_{11}$Cs 537.0373, found 784 537.0373.

Example 4

Methyl 2,4,5,7-tetra-O-acetyl-3-deoxy-α-D-arabino-2-heptulosonate (8).

7: $^1$NMR (D$_2$O) δ 1.773 (1H, dd, J$_{3ax,4}$=11.8, J$_{3ax,3eq}$= 13.0 Hz, H-3ax), 2.180 (1H, dd, J$_{3eq,4}$=5.1, J$_{3eq,3ax}$=13.0 Hz, H-3eq), 3.433 (1H, dd, J$_{5,4}$=9.2, J$_{5,6}$=9.5 Hz, H-5), 3.744 (1H, m, H-7'), 3.930ddd, J$_{6,7}$=3.5, J$_{6,7}$=3.5, J$_{6,7}$=3.5, J$_{6,5}$= 9.5 Hz, H-6) 3.807 (1H, m, H-7), 3.812 (1H, m, H-7'), 3.930 (1H, ddd, J$_{4,3eq}$=5.1, J$_{4,5}$=9.2, J$_{4,3a}$=11.8 Hz, H-4).

8: (50.0 mg, 39% from 0.33 mmol of D-erythrose): [α]$^{25}$D +54.0° (c 0.50, CHCl$_3$); $^1$H NMR (CDCl$_3$) δ 2.034 (3H, s, acetyl), 2.053 (3H, s, acetyl), 2.087 (3H, s, acetyl), 2.087 (1H, dd, J$_{3ax,4}$=11.4, J$_{3ax,3eq}$=13.6 Hz, H-3ax), 2.173 (3H, s, acetyl), 2.658 (1H, dd, J$_{3eq,4}$=5.2 , J$_{3eq,3ax}$=13.6Hz, H-3eq), 3.808 (3H, s, COOCH$_3$), 4.058 (1H, dd, J$_{6,7}$=2.3, J$_{6,7}$=4.3, J$_{6,5}$=10.2 Hz, H-6), 4.100 (1H, J$_{7,6}$=2.3, J$_{7,7}$=12.4 Hz, H-7), 4.355 (1H, J$_{7',6}$=4.3, J$_{7',7}$=12.4 Hz, H-7'); $^{13}$C NMR (CDCl$_3$) δ 20.65, 20.76, 20.76, 20.84, 35.58, 53.31, 61.69, 68.16,, 68.37, 71.51, 97.29, 166.41, 168.43, 169.61, 170.13, 170.77. HRMS (M+Cs$^+$) calcd C$_{16}$H$_{22}$O$_{11}$Cs 523.0216, found 523.0216.

Example 5

Methyl 2,4,5-tri-O-acetyl-2-keto-3-deoxy-α-D-galactonate (10).

9: $^1$H NMR (D$_2$O) δ 1.795 (1H, dd, J$_{3ax,4}$=11.6, J$_{3ax,3eq}$= 13.1 Hz, H-3ax), 2.176 (1H, dd, J$_{3eq,4}$=5.1, J$_{3eq,3ax}$=13.1 Hz, H-3eq), 3.60–3.65 (2H, m), 3.77–3.91 (2H, m).

10: (11.0 mg, 11% from 0.33 mmol of D-glyceraldehyde): [α]$^{25}$D +31.8° (c 1.10, CHCl$_3$); $^1$H NMR (CDCl$_3$) δ 1.948 (1H, dd, J$_{3ax,4}$=11.2, J$_{3ax,3eq}$=13.5 Hz, H-3ax), 2.055 (3H, s, acetyl), 2.059 (3H, s, acetyl), 2.170 (3H, s, acetyl), 2.618 (1H, dd, J$_{3eq,4}$=5.2, J$_{3eq,3ax}$=13.5 Hz, H-3eq), 3.629 (1H, dd, J$_{6ax,5}$=10.6, J$_{6ax,6eq}$=11.3 Hz, H-6ax), 3.809 (3H, s, COOCH$_3$), 4.149 (1H, dd, J$_{6eq,5}$=5.7, J$_{6eq,6ax}$11.3 Hz, H-6eq), 5.049 (1H, ddd, J$_{5,6eq}$=5.7, J$_{5,4}$=9.5, J$_{5,6ax}$=10.6 Hz, H-5), 5.320 (1H, ddd, J$_{4,3eq}$=5.2, J$_{4,5}$=9.5, J$_{4,3ax}$=11.2 Hz, H-4); $^{13}$C NMR (CDCl$_3$) δ 20.67, 20.72, 20.89, 35.81, 53.25, 62.17, 67.66, 68.49, 96.80, 166.96, 168.50, 169.84, 170.05. HRMS (M+Cs$^+$) calcd C$_{13}$H$_{18}$O$_9$Cs 451.0005, found 451.0005.

Example 6

2,4,7-Tri-O-acetyl-3-deoxy-α-D-lyxo-2-heptulosonic acid 1<<5 lactone (12).

11: $^1$H NMR (D$_2$O) δ 1.90–1.98 (m, H-3 of the major component); a minor pair of H-3 protons: 2.072 (dd, J$_{3,4}$= 3.1, J$_{3,3}$=14.2 Hz, H-3), 2.576 (dd, J$_{3',4}$=7.3, J$_{3',3}$=14.2 Hz, H-3'); another minor pair of H-3 protons: 2.301 (dd, J=7.0, 13.4 Hz), 2.384 (dd, J=7.0, 13.4 Hz); 3.60–3.95 (m), 3.95–4.20 (m), 4.48–4.52 (m).

12: (1.9 mg): $^1$H NMR (CDCl$_3$) δ 2.096 (3H, s, acetyl), 2.127 (3H, s, acetyl), 2.180 (3H, s, acetyl), 2.339 (1H, ddd, J$_{3,5}$=0.6, J$_{3,4}$=2.4, J$_{3,3}$=14.9 Hz, H-3), 2.972 (1H, dd, J$_{3',4}$= 9.4, J$_{3,5}$=14.9 Hz, H-3'), 4.180 (1H, ABX type, J$_{6,7}$=5.6, J$_{6,7}$=9.9 Hz, H-6), 4.28–4.35 (2H, m, ABX type, H-7, H-7'), 4.904 (1H, d, J$_{5,4}$=2.0 Hz, H-5), 5.164 (1H, ddd, J$_{4,5}$=2.0, J$_{4,3}$=2.4, J$_{4,3}$=9.4 Hz, H-4) . HRMS (M+Cs$^+$) calcd C$_{13}$H$_{16}$O$_9$Cs 448.9849, found 448.9858.

Example 7

Methyl 2,4,5-tri-O-acetyl-2-keto-3-deoxy-α-L-gluconate (14).

13 (L-KDG): $^1$H NMR (D$_2$O) A major pair of H-3 protons: δ 1.873 (dd, J$_{3eq,4}$=5, J$_{3eq,3ax}$=13.0 Hz, H-3eq), 1.984 (dd, J$_{3ax,4}$=11.9, J$_{3ax,3eq}$=13.0 Hz, H-3ax); a minor pair of H-3 protons: 2.051 (dd, J$_{3,4}$=3.2, J$_{3,3}$=14.1 Hz, H-3), 2.521 (dd, J$_{3',4}$=7.5, J$_{3',3}$=14.1 H-3'); a minor H-3 proton ($^2$C$_5$ β-pyranose form is suggested): 2.167 (dd, J$_{3,4}$=4.0, J$_{3,3}$=13.7 Hz), in this case the H-3' proton could not be specified by overlapping of the signals; another minor pair of H-3 protons: 2.284 (dd, J=6.4, 13.1 Hz), 2.341 (dd, J=6.4, 13.1 Hz); 3.60–4.10 (m), 4.15–4.20 (m), 4.30–4.40 (m).

14: (2.0 mg): $^1$H NMR (CDCl$_3$) δ 2.034 (3H, s, acetyl), 2.150 (3H, s, acetyl), 2.152 (3H, s, acetyl), 2.288 (1H, d, J$_{3ax,4}$=10.1 Hz, H-3ax), 2.292 (1H, dd, J$_{3eq,5}$=0.4 Hz, J$_{3eq,4}$=7.0 Hz, H-3eq), 3.830 (3H, s, COOCH$_3$), 3.999 (1H, dd, J$_{6eq,5}$=1.5, J$_{6eq,6ax}$=13.2 Hz, H-6eq), 4.092 (1H, dd, J$_{6ax,5}$= 2.0, J$_{6ax,6eq}$=13.2 Hz, H-6ax), 5.251 (1J$_{5,3eq}$=0.4, J$_{5,6eq}$=1.5, J$_{5,6ax}$=2.0, J$_{5,4}$=2.7 Hz, H-5), 5.313 (1H, ddd, J$_{4,5}$=2.7, J$_{4,3eq}$=7.0, J$_{4,3ax}$=10.1 Hz, H-4). HRMS (M+Na$^+$) calcd C$_{13}$H$_{18}$O$_9$Na 341.0849, found 341.0849.

Example 8

Methyl 2,4,5,7,8,9-hexa-O-acetyl-3-deoxy-β-L-glycero-galacto-nonulosonate (16).

15 (L-KDN): $^1$H NMR (D$_2$O) δ 1.773 (1H, dd, J$_{3ax,4}$=11.8 Hz, J$_{3ax,3eq}$12.9 Hz, H-3ax), 2.168 (1H, dd, J$_{3eq,4}$=5.1, J$_{3eq,3ax}$=11.8 Hz, H-3eq), 3.579 (1H, dd, J$_{5,4}$=9.3, J$_{5,6}$=9.9 Hz, H-5), 3.654 (1H, dd, J$_{9,8}$=6.3, J$_{9,9}$=11.8 Hz, H-9), 3.766 (1H, ddd, J$_{8,9}$=2.6, J$_{8,9}$=6.3, J$_{8,7}$=9.0 Hz, H-8), 3.831 (1H, dd, J$_{7,6}$=1.1, J$_{7,8}$=9.0 Hz, H-7), 3.873 (1H, dd, J$_{9',8}$=2.6, J$_{9',9}$=11.8 Hz, H-9'), 3.925 (1H, dd, J$_{6,7}$=1.1, J$_{6,5}$=9.9 Hz, H-6), 3.971 (1H, ddd, J$_{4,3eq}$=5.1, J$_{4,5}$=9.3, J$_{4,3ax}$=11.8 Hz, H-4).

16 (108.3 mg, 61% from 0.33 mmol of L-mannose): [α]$^{25}$D +26.3° (c 1.14, CHCl$_3$); $^1$H NMR (CDCl$_3$) δ 2.084 (1H, dd, J$_{3ax,4}$=11.6, J$_{3ax,3eq}$=13.6 Hz, H-3ax), 2.013 (3H, s, acetyl), 2.024 (3H, s, acetyl), 2.040 (3H, s, acetyl), 2.069 (3H, s, acetyl), 2.115 (3H, s, acetyl), 2.157 (3H, s, acetyl), 2.625 (1H, dd, J$_{3eq,4}$=5.3, J$_{3eq,3ax}$=13.6 Hz, H-3eq), 3.790 (3H, s, COOCH$_3$), 4.141 (1H, dd, J$_{9,8}$=5.8, J$_{9,9}$=12.6 Hz, H-9), 4.186 (1H, dd, J$_{6,7}$=2.3, J$_{6,5}$=10.3 Hz, H-6), 4.440 (1H, dd, J$_{9',8}$=2.5, J$_{9',9}$=12.6 Hz, H-9'), 4.975 (1H, dd, J$_{5,4}$=9.6, J$_{5,6}$=10.3 Hz, H-5), 5.150 (1H, ddd, J$_{8,9}$=2.5, J$_{8,9}$5.8, J$_{8,7}$= 6.3 Hz, H-8) , 5.264 (1H, ddd, J$_{4,3}$=5.3, J$_{4,5}$=9.6, H-4), 5.396 (1H, dd, J$_{7,6}$=2.3, J$_{7,8}$=6.3 Hz, H-7); $^{13}$C NMR (CDCl$_3$) δ 20.46, 20.48, 20.58, 20.58, 20.67, 35.32, 53.06, 61.67, 66.68, 67.21, 68.57, 70.00, 71.27, 97.14, 165.91, 168.03, 169.46, 169.57, 169.80, 169.96, 170.41. HRMS (M+Cs$^+$) calcd. C$_{22}$H$_{30}$O$_{15}$Cs 667.0639, found 667.0639.

16': [α]$^{25}$D −26.0° (c 1.00, CHCl$_3$). The $^1$H NMR spectrum was identical with that of 16.

Example 9

2-Deoxy-2-fluoro-D-arabinose (17b).

To a solution of a tribenzoate 17a (available from Pfanstiehl Co., 500 mg, 1.08 mmol) in ethanol (5 mL) was added 10 N NaOH aqueous solution (485 μL, 1.5 eq of each OBz group, total 4.5 eq) at room temperature. After 15 min, H$_2$O (10 mL) and ethanol (5 mL) were added and the mixture was stirred and heated to 50° C. to dissolve the precipitated sodium benzoate. The mixture was further stirred for 1 h at room temperature. After ethanol was evaporated in vacuo, the residue was dissolved in H$_2$O and Dowex 50W-X8 (H$^+$ form) was added to acidify the mixture. The precipitated benzoic acid was filtered off, and the filtrate was treated with Dowex 1-X8 (HCO$_3^-$ form) and filtered, then concentrated in vacuo to give 17b as colorless syrup (153 mg, 94%); $^1$H NMR (D$_2$O) δ 3.60–4.20 (4H, m), 4.337 (ddd, J$_{2,1}$=7.7, J$_{2,3}$=9.3, J$_{2,F}$=51.8 Hz, H-2 of β-anomer), 4.666 (ddd, J$_{2,1}$= 3.7, J$_{2,3}$=9.5, J$_{2,F}$=49.5 Hz, H-2 of α-anomer), 4.763 (dd, J$_{1,F}$=3.3, J$_{1,2}$=7.7, H-1 of β-anomer), 5.434 (dd, J$_{1,F}$=1.5, J$_{1,2}$=3.7 Hz, H-1 of α-anomer). This anomeric mixture was used in the next step without further purification.

Example 10

Methyl 2,4,7,8-tetra-O-acetyl-3,5-dideoxy-5-fluoro-α-D-manno-2-octulosonate (19).

18: $^1$H NMR (D$_2$O) δ 1.814 (dd, J$_{3ax,3eq}$=12.4, J$_{3ax,4}$=12.4 Hz, H-3ax of β-anomer), 1.988 (1H, ddd, J$_{3eq,5}$=0.8, J$_{3eq,4}$=5.6, J$_{3eq,3ax}$=12.9 Hz, H-3eq of α-anomer), 2.058 (1H, dd, J$_{3ax,4}$=11.8, J$_{3ax,3eq}$=12.9 Hz, H-3ax of α-anomer), 2.461 (ddd, J$_{3q,5}$=0.8, J$_{3eq,4}$=5.3, J$_{3eq,3ax}$=12.4 Hz, H-3eq of β-anomer), 3.663 (1H, dd, J$_{8,7}$=5.4, J$_{8,8'}$=12.1 Hz, H-8), 3.828 (1H, dd, J$_{8',7}$=2.4, J$_{8',8}$=12.1 Hz, H-8'), 3.80–3.95 (2H, m), 4.182 (1H, dddd, J$_{4,5}$=2.4, J$_{4,3eq}$=5.6, J$_{4,3ax}$=11.8, J$_{4,F}$=30.5 Hz, H-4), 4.957 (1H, ddd, J$_{5,3eq}$=0.8, J$_{5,4}$=2.4, J$_{5,F}$=50.9 Hz, H-5).

19 (25.3 mg, 18% from 0.33 mmol of 17b): [α]$^{25}$D +96.4° (c 2.53, CHCl$_3$); $^1$H NMR (CDCl$_3$) δ 2.043 (3H, s, acetyl), 2.067 (3H, s, acetyl), 2.131 (3H, s, acetyl), 2.137 (3H, s, acetyl), 2.271 (1H, dd, J$_{3ax,4}$=11.5, J$_{3ax,3eq}$=13.3 Hz, H-3ax), 2.319 (1H, dd, J$_{3eq,4}$=5.9, J$_{3eq,3ax}$=13.3 Hz, H-3eq), 3.805 (3H, s, COOCH$_3$), 4.073 (1H, dd, J$_{6,7}$=9.5, J$_{6,F}$=27.8 Hz, H-6), 4.154 (1H, dd, J$_{8,7}$=3.5, J$_{8,8'}$=12.5 Hz, H-8), 4.601 (1H, dd, J$_{8',7}$=2.2, J$_{8',8}$=12.5 Hz, H-8'), 4.827 (1H, dd, J$_{5,4}$=2.1, J$_{5,F}$=50.9 Hz, H-5), 5.240 (1H, dddd, J$_{4,5}$=2.1, J$_{4,3eq}$=5.9, J$_{4,3ax}$=11.5, J$_{4,F}$=21.3 Hz, H-4), 5.288 (1H, ddd, J$_{7,8}$=2.2, J$_{7,8'}$=3.5, J$_{7,6}$=9.5 Hz, H-7); $^{13}$C NMR (CDCl$_3$) δ 20.56, 20.56, 20.71, 20.83, 30.60, 53.18, 61.46, 66.45, (d, J$_{C,F}$=17.8 Hz), 67.89 (d, J$_{C,F}$=4.1 Hz), 69.60 (d, J$_{C,F}$=18.2 Hz), 83.02 (d, J$_{C,F}$=186.2 Hz), 97.04, 166.49, 167.75, 169.14, 170.18, 170.20. HRMS (M+Cs$^+$) calcd C$_{17}$H$_{23}$O$_{11}$FCs 555.0279, found 555.0288.

Example 11

Larger scale synthesis of 18.

Fluorosugar 17b (340 mg, 2.25 mmol), sodium pyruvate (2.074 g, 28.9 mmol), dithiothreitol (1.7 mg), NaN$_3$ (2.3 mg), phosphate buffer (pH 7.5, 50 mM, 1.12 mL) was added to the enzyme solution (3.0 mL, 24 U). After the pH was adjusted to 7.5, the volume was made up to 10.0 mL. The mixture was stirred under N$_2$ at room temperature for 7 days. The pH was lowered to 2.5 by addition of Dowex 50W-X8 (H$^+$ form) and the mixture was kept at 0° C. for 1 h. The precipitate was removed by centrifugation at 23,000×g for 1 h at 4° C. Before the anion-exchange resin treatment, the excess pyruvate was removed as follows. The mixture was diluted to 80 mL and the pH was adjusted to 6.5 by the addition of 2N aqueous ammonia solution. The antifoam (Antifoam AF emulsion, Dow-Corning Nakaraitesque, 10% emulsion in water, 0.32 mL) and pyruvate decarboxylase (Sigma P 6810, 0.2 mL, 12.5 U) was added and the mixture was stirred at room temperature with bubbling of N$_2$ (1.5 L/min). The pH was monitored and occasionally adjusted between 6.0 and 6.5, by addition of Dowex 50W-X8 (H$^+$ form). The decarboxylase was periodically added to the mixture (each 0.2 mL) at an interval of 30 min, to avoid the denaturation which is caused by the rapid formation of acetaldehyde. The total amount of the enzyme was 3.2 mL (200 U). The reaction mixture was further stirred overnight. Then the mixture was centrifuged, and the supernatant was diluted to 100 mL and applied to a column of Dowex 1-X8 (2050 mesh, bicarbonate form, bed volume, 100 mL).

The pH of the eluent and washings was re-adjusted to 5.5 and further applied to the same column to ensure the adsorption of desired product. After washing with water, the desired product was eluted with a linear gradient from 0 to 0.3M of ammonium bicarbonate. The product was further purified by Biogel P-2 column (bed volume 20 mL) to give 192 mg (33%) of 18. The $^1$H NMR spectrum was identical with the sample mentioned above.

Example 12

Benzyl 2,4,5,7,8-penta-O-acetyl-3-deoxy-α-D-manno-2-octulosonate (20b).

A suspension of KDO ammonium salt monohydrate (160 mg, 0.59 mmol), acetic anhydride (3 mL), pyridine (3 mL), and 4-(N,N-dimethylamino)pyridine (DMAP, 2 mg) was stirred overnight at room temperature. Ice-cooled water was added and the mixture was stirred for 30 min. After dilution with water, the pH of the mixture was adjusted to 3.5 by addition of Dowex 50W-X8 (H$^+$ form). The resin was filtered off, and the filtrate was concentrated in vacuo. The residue was diluted with a mixture of chloroform and toluene and the solvent was evaporated. This procedure was repeated three times to remove trace of water. The residue was dissolved in anhydrous DMF. Benzyl bromide (161 mg, 0.94 mmol), Cs$_2$CO$_3$ (390 mg, 1.20 mmol), and tetrabutylammonium iodide (33 mg) were added and the mixture was stirred for 4 h at room temperature under N$_2$. The mixture was diluted with 0.5N ice-cooled hydrochloric acid and extracted twice with a mixture of diethyl ether and toluene (1:1). The organic layer was successively washed with water, saturated aqueous NaHCO$_3$ and brine, dried over anhydrous Na$_2$SO$_4$ and concentrated in vacuo. The residue was chromatographed over silica gel (20 g). Elution with hexane-diethyl ether (2:11:1) afforded 15b, which was recrystallized from diethyl ether to give 220 mg (70%) as colorless plates, mp 102–103° C. (lit.[26b] mp 98–99° C.); [α]$^{26}$D +293° (c 1.0, CHCl$_3$) [lit.[26b] [α]$^{25}$D +91.9° (c 0.9, CHCl$_3$). Its $^1$H NMR spectrum (CDCl$_3$) was in good accordance with that reported previously by Nakamoto (*Chem. Pharm. Bull.* 1987, 35, 4537). HRMS (M+Na$^+$) calcd 561.1584, found 561.1602.

Example 13

2,4,5,7,8-Penta-O-acetyl-3-deoxy-α-D-manno-2-octulosonic acid (20a).

A mixture of 20b (220 mg, 0.41 mmol) and Pd-C (10%, 55 mg) in ethanol (3 mL) was vigorously stirred under H$_2$ at room temperature for 1 h. After the catalyst was filtered off, the filtrate was concentrated in vacuo. The residue was recrystallized from diethyl ether to give 20a (177 mg, 97%) as fine needles, mp 132–133° C.; [α]$^{25}$D +374° (c 0.88, CHCl$_3$). Its $^1$H NMR spectrum (C$_6$D$_6$) was identical with that reported previously by Unger et al. (*Carbohydr. Res.* 1980, 80, 191).

Example 14

1,3,4,6,7-Penta-O-acetyl-2-deoxy-β-D-manno-heptose (21)

To a solution of acid chloride prepared from 20a (30 mg, 0.067 mmol) in toluene was added dropwise a solution of N-hydroxythiopyridone 22 (11 mg, 0.09 mmol) and DMAP (2 mg) in toluene (0.5 mL) and pyridine (0.3 mL) at room temperature under $N_2$ in the dark. After stirring for 10 min, t-butylmercaptane (0.5 mL) was added and the mixture was irradiated with white light (tungsten lamp, 100 W) at room temperature. After stirring for 10 min, $N_2$ was introduced to the mixture under a slightly reduced pressure to remove residual t-butylmercaptane for 30 min. Usual workup and purification by silica gel preparative TLC [developed with hexane-$Et_2O$ (1:1)] afforded 21 (18.5 mg, 68%) as an oil, $[\alpha]^{22}D$ +36.8° (c 1.85, $CHCl_3$); $^1H$ NMR ($CDCl_3$) δ 2.000–2.150 (2H, m, H-2ax, H-2eq), 2.010 (6H, s, acetyl), 2.082 (3H, s, acetyl), 2.119 (3H, s, acetyl), 2.137 (3H, s, acetyl), 3.882 (1H, dd, $J_{5,4}$=1.5, $J_{5,6}$=10.0 Hz, H-5), 4.115 (1H, dd, $J_{7',6}$=4.5, $J_{7',7}$=12.5 H, H-7'), 4.437 (1H, dd, $J_{7,6}$= 2.5, $J_{7,7}$=12.5 Hz, H-7), 5.073 (1H, ddd, $J_{3,4}$=3.0, $J_{3,2eq}$=5.0, $J_{3,2ax}$=12.5 Hz, H-3), 5.165 (1H, ddd,$J_{6,7}$=2.5, $J_{6,7'eq}$=4.5, $J_{6,5}$=10.0 Hz, H-6), 5.303 (1H, dd, $J_{4,5}$=1.5, $J_{4,3}$=3.0Hz, H-4), 5.748 (1H, dd, $J_{1,2eq}$=3.0, $J_{1,2ax}$=10.0 Hz, H-1); $^{13}C$ NMR ($CDCl_3$) δ 20.59, 20.59, 20.65, 20.65, 20.84, 30.35, 62.26, 63.84, 67.32, 67.90, 71.62, 91.67, 168.60, 169.60, 169.83, 170.30, 170.54. HRMS (M+Cs$^+$) calcd $C_{17}H_{24}O_{11}Cs$ 537.0373, found 537.0359.

Example 15
4-Acetamido-1,3,6,7,8-Penta-O-acetyl-2,4-dideoxy-α-D-glycero-D-galacto-octose (24).

A 25 mL two-necked flask equipped with septum, microscale Dean-Stark trapp which was filled with molecular sieves 4A, and a reflux condenser, was used as the reaction vessel. A mixture of 23a (35.0 mg, 0.07 mmol), DMAP (12.3 mg, 1.5 eq), 22 (41.0 mg, 5.0 eq), triethylamine (19 μL) in $CH_2C_2$ (1 mL) was placed in the flask as above. To this was successively added a solution of WSCI-Cl (20 mg) in $CH_2C_2$ (1 mL) and t-butylmercaptane (0.5 mL). The mixture was stirred and irradiated with white light (tungsten lamp, 100 W) at room temperature for 5 h. The reaction was worked up in a similar manner as described above. The crude product was purified by silica gel preparative TLC [developed with ethyl acetate-tetrahydrofuran (1:1)] to give 24 (8.7 mg, 27% from 23a) as an oil, $[\alpha]^{22}D$ +21.3° (c 2.87, $CHCl_3$); $^1H$ NMR ($CDCl_3$) δ 1.908 (3H, s, N-acetyl), 1.915 (1H, ddd, $J_{2ax,1}$= 10.3, $J_{2ax,3}$=11.5, $J_{2ax,2eq}$=12.4 Hz, H-2ax), 2.043 (3H, s, O-acetyl), 2.051 (3H, s, O-acetyl), 2.102 (3H, s, O-acetyl), 2.107 (3H, s, O-acetyl), 2.134 (3H, s, O-acetyl), 2.219 (1H, ddd, $J_{2eq,1}$=2.1, $J_{2eq,3}$=4.9, $J_{2eq,2ax}$=12.4 Hz, H-2eq), 3.764 (1H, dd, $J_{5,6}$=2.4, $J_{5,4}$=10.4 Hz, H-5), 4.023 (1H, dd, $J_{8,7}$= 5.5, $J_{8,8'}$=12.6 Hz, H-8), 4.062 (1H, ddd, $J_{4,NH}$=10.0, $J_{4,3}$= 10.3, $J_{4,5}$=10.4 Hz, H-4), 4.389 (1H, dd, $J_{8',7}$=2.6, $J_{8',8}$=12.6 Hz, H-8'), 5.127 (1H, ddd, $J_{7,8'}$=2.6, $J_{7,8}$=5.5, $J_{7,6}$7.3Hz, H-7), 5.058 (1H, ddd, $J_{3,2}$=4.9, $J_{3,4}$=10.3, $J_{3,2ax}$=11.5 Hz, H-3), 5.190 (1H, d, $J_{NH,4}$=10.0 Hz, NH), 5.391 (1H, dd, $J_{6,7}$=7.3, $J_{6,5}$=2.4 Hz, H-6), 5.646 (1H, dd, $J_{1,2eq}$=2.1, $J_{1,2ax}$= 10.3 Hz, H-1); $^{13}C$ NMR ($CDCl_3$) δ 20.70, 20.70, 20.75, 20.83, 20.83, 23.15, 35.09, 49.22, 61.98, 67.11, 70.23, 70.23, 73.67, 91.19, 168.75, 169.90, 170.12, 170.36, 170.59, 170.88. HRMS (M+Cs$^+$) calcd $C_{20}H_{29}O_{12}NCs$ 608.0744, found 608.0750.

Example of Synthetic Methods Employing Further Aldloases

Example 16

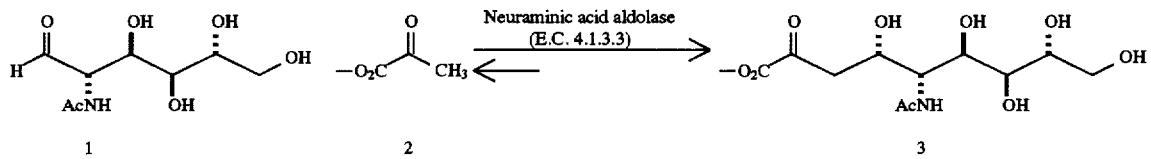

Synthesis of Neuraminic acid (ketoaldonic acid 3) Aldose 1 (1.0 equiv., Whitesides et. Al. *J. Am. Chem. Soc.* 1988,110, 7159), sodium pyruvate 2 (12.8 equiv., Aldrich Chemical company), dithiothreitol (0.5 mol%), $NaN_3$ (0.02 equiv.) and phosphate buffer (pH 7.5, 50mM) is added to the Neuraminic acid aldolase solution (24 U, Whitesides et. Al. *J. Am. Chem. Soc.* 1988,110, 7159). After the pH is adjusted to 7.5, the volume is made up to (5.0 mM). The mixture is stirred under $N_2$ at room temperature for 7 days. The pH is lowered to 2.5 by addition of Dowex 50W-X8 (H$^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 (H$^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the Neuraminic acid product is eluted with a linear gradient from 0 to 0.3M of ammonium bicarbonate. The product is further purified by Biogel P-2 column.

Example 17

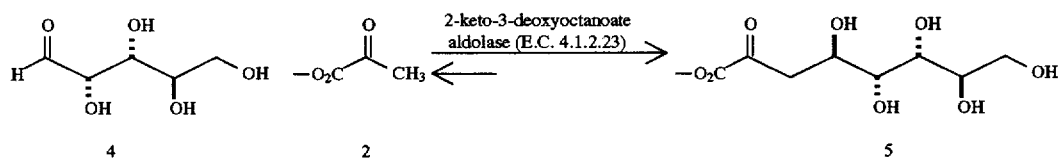

Synthesis of 2-keto-3-deoxyoctanoate (ketoaldonic acid 5)

Aldose 4 (1.0 equiv, Ghalambor et. al., *J. Biol. Chem.* 1966, 241, 3222), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the 2-keto-3-deoxyoctanoate aldolase solution (24 U, Ghalambor et. al., *J. Biol. Chem.* 1966, 241, 3222). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min. to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxyoctanoate product is eluted with a linear gradient from 0 to 0.3M of ammonium bicarbonate. The product is further purified by Biogel P-2 column.

Synthesis of 2-keto-3-deoxy-6-phosphogluconate (ketoaldonic acid 7)

Aldose 6 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the 2-keto-3-deoxy-6-phosphogluconate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min. to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-6-phosphogluconate product is eluted with a linear gradient from 0 to 0.3M of ammonium bicarbonate. The product is further purified by Biogel P-2 column.

Example 18

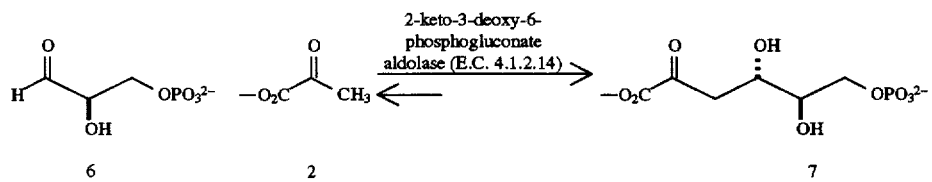

Example 19

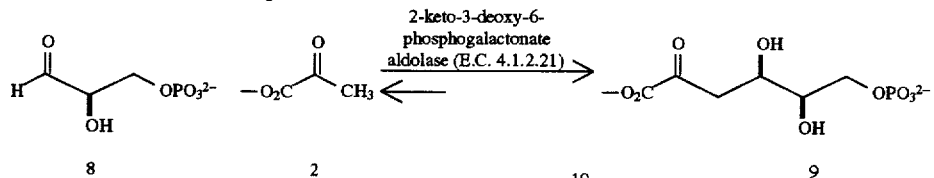

Synthesis of 2-keto-3-deoxy-6-phosphogalactonate (ketoaldonic acid 9)

Aldose 8 (1.0 equiv., Wood et. al., In *The Enzymes; Boyer, P.D. Ed.; Academic: New York,* 1970; Vol VII, 281), sodium pyruvate 2 (12.8 equiv., Aldrich chemical company), dithiothreitol (0.5 mol%), NaN$_3$ (0.02 equiv.) and phosphate buffer (pH 7.5, 50 mM) is added to the 2-keto-3-deoxy-6-phosphogalactonate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under N$_2$ at room temperature for 7 days. The pH is lowered to 2.5 by addition of Dowex 50W-X8 (H$^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03 M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of N$_2$ (1.5 L/min). The pH is monitored an occasionally adjusted between 6.0 and 6.5, by addition of Dowex 50W-X8 (H$^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-6-phosphogalactonate product 9 is eluted with a linear gradient from 0 to 0.3M of ammonium bicarbonate. The product is further purified by Biogel P-2 column.

Synthesis of 2-keto-3-deoxy-D-glucarate (ketoaldonic acid 11)

Aldose 10 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), NaN$_3$ (0.02 equiv.) and phosphate buffer (pH 7.5, 50 mM) is added to the 2-keto-3-deoxy-D-glucarate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under N$_2$ at room temperature for 7 days. The pH is lowered to 2.5 by addition of Dowex 50W-X8 (H$^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of N$_2$ (1.5 L/min). The pH is monitored an occasionally adjusted between 6.0 and 6.5, by addition of Dowex 50W-X8 (H$^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-D-glucarate product is eluted with a linear gradient from 0 to 0.6M of ammonium bicarbonate. The product is further purified by Biogel P-2 column.

Example 20

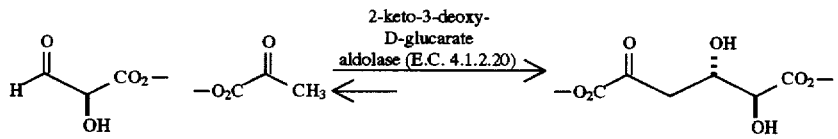

Example 21

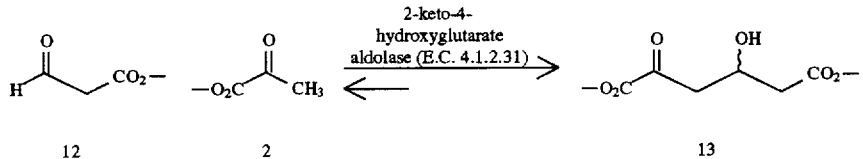

Synthesis of 2-keto-4-hydroxyglutarate (ketoaldonic acid 13)

Aldose 12 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), NaN$_3$ (0.02 equiv.) and phosphate buffer (pH 7.5, 50 mM) is added to the 2-keto-4-hydroxyglutarate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under N$_2$ at room temperature for 7 days. The pH is lowered to 2.5 by addition of Dowex 50W-X8 (H$^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of N$_2$ (1.5 L/min). The pH is monitored an occasionally adjusted between 6.0 and 6.5, by addition of Dowex 50W-X8 (H$^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-4-hydroxyglutarate product 13 is eluted with a linear gradient from 0 to 0.6M of ammonium bicarbonate. The product is further purified by Biogel P-2 column.

Synthesis of 4-methyl-4-hydroxy-2-ketoglutarate (ketoaldonic acid 14)

Aldose 2 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), NaN$_3$ (0.02 equiv.) and phosphate buffer (pH 7.5, 50 mM) is added to the 4-methyl-4-hydroxy-2-ketoglutarate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under N$_2$ at room temperature for 7 days. The pH is lowered to 2.5 by addition of Dowex 50W-X8 (H$^+$ form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of N$_2$ (1.5 L/min). The pH is monitored an occasionally adjusted between 6.0 and 6.5, by addition of Dowex 50W-X8 (H$^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 4-methyl-4-hydroxy-2-ketoglutarate 14 is eluted with a linear gradient from 0 to 0.6M of ammonium bicarbonate. The product is further purified by Biogel P-2 column.

Example 22

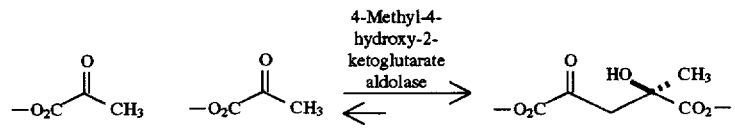

Example 23

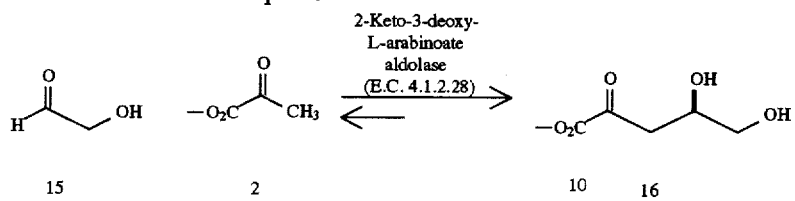

Synthesis of 2-keto-3-deoxy-L-arabinoate (ketoaldonic acid 16)

Aldose 15 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the 2-keto-3-deoxy-L-arabinoate aldolase solution (24 U, Wood et. al., In *The Enzymes*; Boyer, P. D. Ed.; Academic: New York, 1970; Vol VII, 281). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-L-arabinoate 16 is eluted with a linear gradient from 0 to 0.3M of ammonium bicarbonate. The product is further purified by Biogel P-2 column.

Synthesis of 2-keto-3-deoxy-D-pentanoate (ketoaldonic acid 18)

Aldose 17 (1.0 equiv., Dahms, et. al., *Biochem. Biophys. Res. Commun.* 1974, 60, 1433), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the 2-keto-3-deoxy-D-pentanoate aldolase solution (24 U, Dahms, et. al., *Biochem. Biophys. Res. Commun.* 1974, 60, 1433). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-D-pentanoate 18 is eluted with a linear gradient from 0 to 0.3M of ammonium bicarbonate. The product is further purified by Biogel P-2 column.

Example 24

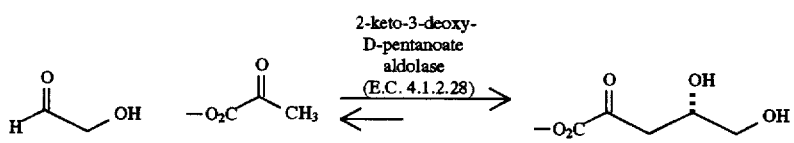

Example 25

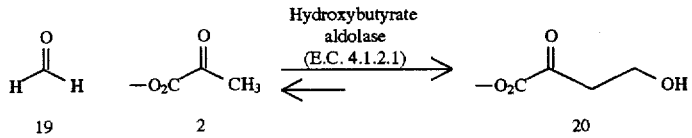

Synthesis of Hydroxybutyrate (ketoaldonic acid 20)

Aldose 19 (1.0 equiv., Hift et. al., *J. Biol. Chem.*, 1952, 198, 901), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the hydroxybutyrate aldolase solution (24 U, Hift et. al., *J. Biol. Chem.*, 1952, 198, 901). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then the mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the Hydroxybutyrate 20 is eluted with a linear gradient from 0 to 0.3M of ammonium bicarbonate. The product is further purified Biogel P-2 column.

Example 26

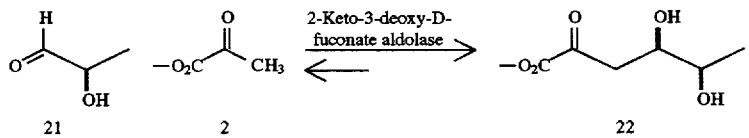

Synthesis of 2-keto-3-deoxy-D-fuconate (ketoaldonic acid 22)

Aldose 21 (1.0 equiv., Wood et. al., In *The Enzymes*; Boyer, P.D. Ed.; Academic: New York, 1970; Vol VII, 281), sodium pyruvate 2 (12.8 equiv., Aldrich chemical company), dithiothreitol (0.5 mol%), $NaN_3$ (0.02 equiv.) and phosphate buffer (pH 7.5, 50 mM) is added to the 2-keto-3-deoxy-D-fuconate aldolase solution (24 U, Wood et. al., In *The Enzymes*; Boyer, P.D. Ed.; Academic: New York, 1970; Vol VII, 281). After the pH is adjusted to 7.5, the volume is made up to (5.0 mM). The mixture is stirred under $N_2$ at room temperature for 7 days. The pH is lowered to 2.5 by addition of Dowex 50W-X8 ($H^+$form) and the mixture is kept at 0° C.; 1 hour. The precipitate is removed by centrifugation at 23,000×g for 1 hour at 4° C.

Before the anion-exchange resin treatment, the excess pyruvate is removed as follows: The mixture is diluted to (0.03M, based on initial aldose concentration) and the pH is adjusted to 6.5 by the addition of 2N aqueous ammonia solution. The antifoam (Antifoam AF emulsion, Dow-Corning Nakaraitesque, 10% emulsion in water, 7.0M, based on aldose) and pyruvate decarboxylase (Sigma P 6810, 12.5 U) is added and the mixture is stirred at room temperature with bubbling of $N_2$ (1.5 L/min). The pH is monitored an occasionally adjusted between 6.0 and 6.5, by addition of Dowex 50W-X8 ($H^+$) form. The decarboxylase is periodically added to the mixture (each 12.5 U) at an interval of 30 min, to avoid the denaturation which is caused by the rapid formation of acetaldehyde. The total amount of the enzyme is 200 U. The reaction mixture is further stirred overnight. Then ie mixture is centrifuged and the supernatant is diluted to 100 mL and applied to a column of Dowex 1-X8 (20–50 mesh, bicarbonate form, bed volume, 22.5 mM, based on initial aldose concentration). The pH of the eluent and washings is re-adjusted to 5.5 and further applied to the same column to ensure the adsorption of desired product. After washing with water, the 2-keto-3-deoxy-D-fuconate aldolase 22 product is eluted with a linear gradient from 0 to 0.3M of ammonium bicarbonate. The product is further purified by Biogel P-2 column.

Further Examples

Other preferred aldolases include the following: 2-dehydro-3-deoxy-L-pentonate aldolase (EC: 4.1.2.18); and 4- (2-carboxyphenyl)-2-oxobut-3-enoate aldolase (EC: 4.1.2.34).

Other potential aldolases employable in this protocal include the following: ketotetrose-phosphate aldolase (EC: 4.1.2.2); pentosealdolase (EC: 4.1.2.3); deoxyribose-phosphate aldolase (EC: 4.1.2.4); threonine aldolase (EC: 4.1.2.5); phosphoketolase (EC: 4.1.2.9); ketopantoaldolase (EC: 4.1.2.12); fructose-bisphosphate aldolase (EC: 4.1.2.13); 2-dehydro-3-deoxyphosphoheptonate aldolase (EC: 4.1.2.15); 2-dehydro-3-deoxyphosphooctonate aldolase (EC: 4.1.2.16); L-fuculose-phosphate aldolase (EC: 4.1.2.17); rhamnulose-1-phosphate aldolase (EC: 4.1.2.19); dimethylaniline-N-oxide aldolase (EC: 4.1.2.24); dihydroneopterin aldolase (EC: 4.1.2.25); phenylserine aldolase (EC: 4.1.2.26); sphinganine-1-phosphate aldolase (EC: 4.1.2.27); 5-dehydro-2-deoxyphosphogluconate aldolase (EC: 4.1.2.29); 17α-hydroxyprogesterone aldolase (EC:

4.1.2.30); trimethylamine-oxide aldolase (EC: 4.1.2.32); lactate aldolase (EC: 4.1.2.36); benzoin aldolase, (EC: 4.1.2.38).

What is claimed is:

1. A process for synthesizing a 2-ketoaldonic acid that comprises:

(a) admixing an excess of (I) pyruvate, (ii) an aldolase selected from the group consisting of, 2-keto-3-deoxyoctanoate aldolase, 2-keto-3-deoxy-6-phosphogluconate aldolase, 2-keto-3-deoxy-6-phosphogalactonate aldolase, 2-keto-3-deoxy-D-glucarate aldolase, 2-keto-4-hydroxyglutarate aldolase, 4-methyl-4-hydroxy-2-ketoglutarate aldolase, 2-keto-3-deoxy-L-arabinoate aldolase, 2-keto-3-deoxy-D-pentanoate aldolase, hydroxybutyrate aldolase, 2-keto-3-deoxy-D-fuconate aldolase, 2-dehydro-3-deoxy-L-pentonate aldolase, 4-(2-carboxyphenyl)-2-oxobut-3-enoate aldolase, ketotetrose-phosphate aldolase, pentosealdolase, deoxyribose-phosphate aldolase, threonine aldolase, phosphoketolase, ketopantoaldolase, fructose-bisphosphate aldolase, 2-dehydro-3-deoxyphosphoheptonate aldolase, 2-dehydro-3-deoxyphosphooctonate aldolase, L-fuculose-phosphate aldolase, rhamnulose-1-phosphate aldolase, dimethylaniline-N-oxide aldolase, dihydroneopterin aldolase; phenylserine aldolase; sphinganine-1-phosphate aldolase, 5-dehydro-2-deoxyphosphogluconate aldolase, 17α-hydroxyprogesterone aldolase, trimethylamine-oxide aldolase, lactate aldolase, benzoin aldolase, and (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a 2-ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed 2-ketoaldonic acid.

2. A process for synthesizing a ketoaldonic acid that comprises:

(a) admixing an excess of (I) pyruvate, (ii) 2-keto-3-deoxyoctanoate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

3. A process for synthesizing a ketoaldonic acid as described in claim 2 wherein:

the acceptor substrate aldose is the compound represented by the following structure:

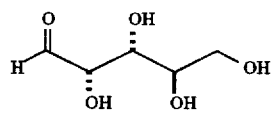

and the ketoaldonic acid is represented by the following structure:

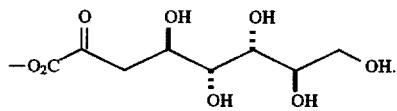

4. A process for synthesizing a ketoaldonic acid that comprises:

(a) admixing an excess of (I) pyruvate, (ii) 2-keto-3-deoxy-6-phosphogluconate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

5. A process for synthesizing a ketoaldonic acid as described in claim 4 wherein:

the acceptor substrate aldose is the compound represented by the following structure:

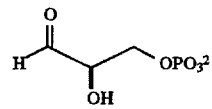

and the ketoaldonic acid is represented by the following structure:

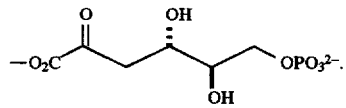

6. A process for synthesizing a ketoaldonic acid that comprises:

(a) admixing an excess of (I) pyruvate, (ii) 2-keto-3-deoxy-6-phosphogalactonate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

7. A process for synthesizing a ketoaldonic acid as described in claim 6 wherein:

the acceptor substrate aldose is the compound represented by the following structure:

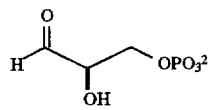   8 and the ketoaldonic acid is represented by the following structure:

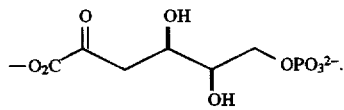   9

8. A process for synthesizing a ketoaldonic acid that comprises:

(a) admixing an excess of (I) pyruvate, (ii) 2-keto-3-deoxy-D-glucarate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

9. A process for synthesizing a ketoaldonic acid as described in claim 8 wherein:

the acceptor substrate aldose is the compound represented by the following structure:

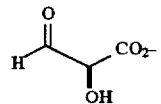   10 and the ketoaldonic acid is represented by the following structure:

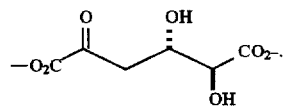   11

10. A process for synthesizing a ketoaldonic acid that comprises:

(a) admixing an excess of (I) pyruvate, (ii) 2-keto-4-hydroxyglutarate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

11. A process for synthesizing a ketoaldonic acid as described in claim 10 wherein:

the acceptor substrate aldose is the compound represented by the following structure:

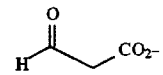   12 and the ketoaldonic acid is represented by the following structure:

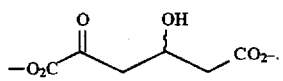   13

12. A process for synthesizing a ketoaldonic acid that comprises:

(a) admixing an excess of (I) pyruvate, (ii) 4-methyl-4-hydroxy-2-ketoglutarate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

13. A process for synthesizing a ketoaldonic acid as described in claim 12 wherein:

the acceptor substrate aldose is the compound represented by the following structure:

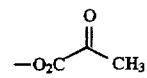   2 and the ketoaldonic acid is represented by the following structure:

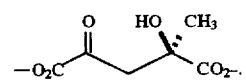   14

14. A process for synthesizing a ketoaldonic acid that comprises:

(a) admixing an excess of (I) pyruvate, (ii) 2-keto-3-deoxy-L-arabinoate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

15. A process for synthesizing a ketoaldonic acid as described in claim 14 wherein:

the acceptor substrate aldose is the compound represented by the following structure:

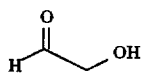
15 and the ketoaldonic acid is represented by the following structure:

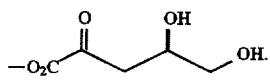
16

16. A process for synthesizing a ketoaldonic acid that comprises:

(a) admixing an excess of (I) pyruvate, (ii) 2-keto-3-deoxy-D-pentanoate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

17. A process for synthesizing a ketoaldonic acid as described in claim 16 wherein:

the acceptor substrate aldose is the compound represented by the following structure:

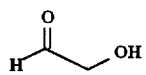
17 and the ketoaldonic acid is represented by the following structure:

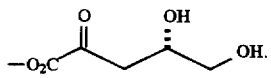
18

18. A process for synthesizing a ketoaldonic acid that comprises:

(a) admixing an excess of (I) pyruvate, (ii) hydroxybutyrate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

19. A process for synthesizing a ketoaldonic acid as described in claim 18 wherein:

the acceptor substrate aldose is the compound represented by the following structure:

19 and the ketoaldonic acid is represented by the following structure:

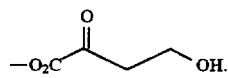
20

20. A process for synthesizing a ketoaldonic acid that comprises:

(a) admixing an excess of (I) pyruvate, (ii) 2-keto-3-deoxy-D-fuconate aldolase, (iii) an acceptor substrate aldose for said aldolase in an aqueous solvent to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylase into the reaction mixture to form a further admixture;

(d) maintaining said further admixture for a time period and under biological reaction conditions sufficient for the excess pyruvate to decompose; and (e) recovering the formed ketoaldonic acid.

21. A process for synthesizing a ketoaldonic acid as described in claim 20 wherein:

the acceptor substrate aldose is the compound represented by the following structure:

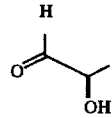
21 and the ketoaldonic acid is represented by the following structure:

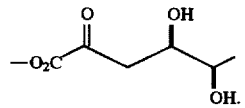
22

* * * * *